United States Patent [19]
Niikura

[11] Patent Number: 6,128,093
[45] Date of Patent: Oct. 3, 2000

[54] UNIT FOR MEASURING OPTICAL PROPERTIES

[75] Inventor: Hiroshi Niikura, Chigasaki, Japan

[73] Assignee: Nikon Corporation, Tokyo, Japan

[21] Appl. No.: 09/414,075

[22] Filed: Oct. 7, 1999

[30] Foreign Application Priority Data

| Oct. 8, 1998 | [JP] | Japan | 10-286557 |
| Aug. 16, 1999 | [JP] | Japan | 11-229763 |

[51] Int. Cl.[7] .................................................. G01N 21/00
[52] U.S. Cl. .......................... 356/432; 356/369; 356/319; 356/326; 356/445
[58] Field of Search ..................................... 356/364–369, 356/445–448, 319, 326, 327, 322, 432, 436, 440, 451, 452, 453

[56] References Cited

U.S. PATENT DOCUMENTS

| 3,499,716 | 3/1970 | Bennett . | |
| 3,642,375 | 2/1972 | Macek . | |
| 4,070,112 | 1/1978 | Tsunazawa et al. . | |
| 4,210,401 | 7/1980 | Batten | 356/369 |
| 4,790,659 | 12/1988 | Erman et al. | 356/369 |
| 4,834,539 | 5/1989 | Le Bris et al. | 356/369 |
| 4,945,254 | 7/1990 | Robbins | 356/445 |
| 5,106,196 | 4/1992 | Brierley | 356/445 |
| 5,880,831 | 3/1999 | Buermann et al. | 356/319 |
| 5,910,842 | 6/1999 | Piwonka-Corle et al. | 356/369 |
| 5,917,594 | 6/1999 | Norton | 356/369 |

*Primary Examiner*—Hoa Q. Pham
*Attorney, Agent, or Firm*—Morgan, Lewis & Bockius LLP

[57] ABSTRACT

A unit for measuring optical properties. The unit includes the first through sixth reflecting surfaces, a reflecting surface rotating device and an object moving device. In order to accurately measure transmittance, reflectance and phase change in transmittance or reflection of optical elements, especially transmittance of a thick object, the first through the fourth reflecting surfaces M1–M4 are arranged so that an optical path formed by the reflecting surfaces M1–M4 has a shape like an "N" letter and so that light of incidence L1 has the same optical axis as exit light L2. An optical center O is a point that a line segment that connects a point of incidence A with an exit point D intersects an optical path that connects the reflecting surface M2 with the reflecting surface M3. The reflecting surface M2 is an ellipsoid of revolution having foci of the optical center O and the point of incidence A. The reflecting surface M3 is an ellipsoid of revolution having foci of the optical center and the exit point D. A reflecting surface rotating device rotates M4 at the exit point D in conjunction with the reflecting surface M1 that is rotated at the point of incidence A. The reflecting surface M5 is a parabolic mirror that makes light reflected from the reflecting surface M1 parallel. M6 is a parabolic mirror that converges light reflected from the reflecting surface M5 onto the reflecting mirror M4.

15 Claims, 23 Drawing Sheets

ELLIPTICAL FACTOR

SPHERICAL FACTOR

CYLINDRICAL SURFACE

UNIT FOR MEASURING OPTICAL PROPERTIES

This application claims the benefit of Japanese Applications No. 10-286557, filed in Japan on Oct. 8, 1998, and No. 11-229763, filed in Japan on Aug. 16, 1999, both of which are hereby incorporated by reference.

BACKGROUND OF THE INVENTION

1. Field of the Invention

This invention relates to a unit for measuring optical properties of optical elements. The optical properties such as transmittance, reflectance, phase change in transmission or reflection are measured.

2. Background of the Related Art

It is well known that typical optical properties of optical elements include transmittance and reflectance. The transmittance and the reflectance respectively include relative transmittance and relative reflectance that are defined as a relative value of an object to a predetermined value of a reference object. The transmittance and the reflectance also include respectively absolute transmittance and absolute reflectance that are determined by measuring the object itself. The transmittance change and the reflectance that change with respect to wavelength are called spectral transmission factor and spectral reflection factor, respectively.

In order to measure the transmittance or the reflectance, generally, the spectral transmission factor or the spectral reflection factor is measured, and also, the transmittance or the reflectance with respect to angle of incidence is considerably often measured.

Another optical properties of the optical elements include refractive index of materials of the optical elements, and optical constant of thin film. The refractive index and the optical constant are generally obtained by measuring phase change dependence on angle of incidence, which is caused when light passes through an object, and by analyzing the measured phase change (hereafter this phase change is called "phase change in transmission"). The refractive index and the optical constant are also obtained by measuring phase change dependence on angle of incidence, which is caused when light is reflected by the object, and by analyzing the measured phase change (hereafter this phase change is called "phase change in reflection").

The transmittance and the reflectance are commonly measured by a commercial spectrophotometer along with an attached special optical system. The phase change in transmission and reflection is commonly measured by an ellipsometer. The following explain these conventional apparatus.

The conventional apparatus measure the transmittance of the optical elements using the spectrophotometer, considering the dependence on the angle of incidence, as described below. FIG. 25 shows a conventional apparatus, but the details of the spectrophotometer, i.e., a monochromator portion and a light receptor, are not shown.

In this conventional apparatus, an object 11 is set on a goniometer 13, and the object 11 is rotated predetermined degrees on the goniometer 13. The amount of light that has past through the object 11 (the amount of light to be measured) is measured, changing an angle of the incident light θ. The reference amount of light is measured in a state that the object 11 is not set on the goniometer 13. From the measured amount of light and reference amount of light, the transmittance dependence on an angle of incidence can be measured.

A conventional apparatus using so-called VN method that is written in Japanese Industrial Standard JISK 0115-1992 is known as an apparatus for measuring the absolute reflectance of an optical element. FIGS. 26(A) and 26(B) explain this apparatus.

The VN method uses three mirrors, M1, M2 and M3. These mirrors M1 through M3 are arranged so that an optical path extending from the mirrors M1 through M3 is formed like a "V" letter (FIG. 26(A)), and this stat is called the first state. The amount of light output from the optical system (the reference amount of light) is measured by the light receptor (not shown). The reference amount of light lr is $$lr = lo \times R1 \times R2 \times R3$$

where lo is the amount of incident light, R1 through R3 are reflectances of mirror M1 through M3, respectively.

Then, the object 11 is inserted onto the optical path of the optical system, as shown in FIG. 26(B). The mirrors M1 through M3 are moved and rotated so that the object 11 and Mirrors M1 through M3 produce an optical path like an "N" letter. The amount of light output from the optical system (the amount of light to be measured) is measured by the light receptor. The amount of light is $$ls = R1 \times R2 \times R3 \times Rs$$

where Rs is the absolute reflectance of the surface of the object 11.

Since the amount of light to be measured is the product of the reference amount of light and the absolute reflectance of the object, the absolute reflectance of the object Rs is $$Rs = ls/lr$$

When the transmittance or reflectance is measured, the accuracy of measurement is increased by adopting a double-beam method. In the double-beam method, a light beam from a light-source is divided into two beams: one beam travels an optical path including the object, another travels an optical path including the light receptor. By monitoring the optical path including the light receptor, information such as the intensity fluctuations of the light source is measured, thereby correcting measured values of the object and increasing the accuracy of measurement.

The conventional apparatus for measuring the relative reflectance include the following apparatus. Referring to FIGS. 27(A) and 27(B), Mirrors M1 and M2 are inclined each other so as to form a shape like a gable roof. The reflecting surfaces of mirrors M1 and M2 are turned outward each other, resulting in the reflecting surfaces of the two mirrors being directed upward. A reference object 15 (as shown in FIG. 27(A)) or an object 11 (as shown in FIG. 27(B)) is placed above the mirrors M1 and M2. The light beam impinges on the Mirror M1 and is reflected by the same and travels to the reference object 15. And the light beam is reflected by the reference object 15 (or the object 11) and travels to the Mirror M2. After the light beam is reflected by the mirror M2, it travels to the light receptor (not shown). The light receptor measures lr, i.e., the amount of light, when the reference object 15 is placed above the mirrors M1 and M2, and measures ls, i.e., the amount of light, when the object 11 is placed above the mirrors M1 and M2. The relative reflectance is determined by Rs=ls/lr, as well as the previously-mentioned absolute reflectance.

In the case of performing ellipsometry using ellipsometer, since it is necessary to irradiate light to the object in an arbitrary angle and to receive the reflected light from the object, the following configuration is used as shown in FIG. 28.

The object 11 is placed on a goniostage 17 of the ellipsometer. A light source unit 19 is fixed. The light source unit 19 includes a light source 19a, a wave filter 19b, a light-collecting optical system 19c and a polarizer 19d. The light receptor 21 is fixed to a stage 23 that rotates about the same rotating axis as that of the goniostage 17, with rotation of the stage 23 being synchronized with rotation of the goniostage 17. The light receptor 21 includes an analyzer 21a, light-collecting system 21b and a light-receiving element 21c. The angle of incidence on a surface 11a of the object 11 is changed by rotating the goniostage 17. When the angle of incidence is θ, the stage 23, on which the light receptor 21 is mounted, receives the reflected light from the object 11 after the stage 23 rotates 2θ degrees. Thus, it is possible to perform photometry by changing an angle of incidence.

To calculate the phase change of light from information measured using ellipsometer, it is necessary to use the specific method and calculation theory of ellipsometry. Although the method and calculation are described in reference 1 ("Optical Measurement Handbook" by Toshiharu Takou, Asakura book publishing), explanations of them are omitted because they are not directly related to the present invention.

However, the above-described devices for measuring optical properties have the following problems. One problem is that the absolute reflectance measuring apparatus as shown FIG. 26 cannot change the angle of incidence to measure the reflectance. To solve this problem, it is necessary, every time measurement is performed, to prepare the VN optical system having a different angle of incidence. However, even if such a VN optical system is prepared, the reflectance can be measured at a merely discrete angle of incidence. Thus, the conventional device cannot measure the reflectance at an arbitrary angle of incidence, and cannot change the angle of incidence continuously to measure the reflectance.

Another problem is that the relative reflectance measuring apparatus, as shown in FIG. 27, also cannot change the angle of incidence to measure the reflectance. To solve this problem, it is necessary to prepare an optical system shaped like a gable roof every time the angle of incidence is changed. However, even if the optical system shaped like the gable roof is prepared every time the angle of incidence is changed, the reflectance can be measured at a merely discrete angle of incidence. Thus, the conventional devices cannot measure the reflectance at an arbitrary angle of incidence, and cannot change an angle of incidence continuously to measure the reflectance.

Furthermore, as to both apparatus as shown in FIGS. 26 and 27, the VN optical system or the optical system shaped like the gable roof must be exchanged every time the angle of incidence is changed, and the exchanged optical system must be adjusted. This causes a problem that optical properties, such as optical path difference, aberration, focal length and quantity of light, could be changed, strictly speaking.

Furthermore, using an ellipsometer could cause instability of measurement because of mechanical causes, because it is necessary for a mechanical structure to move the light receptor while moving the object. Moving the light receptor to a different position could make it difficult to achieve high accuracy of measurement, because magnetic field distribution could affect adversely. Furthermore, because of above-mentioned mechanical structure, a larger space is necessary for installing the apparatus.

Furthermore, the essential disadvantage of the ellipsometer is that it cannot perform double beam measurement. Accordingly, it cannot compensate fluctuation of intensity of light of the light source, or fluctuation of intensity of polarized light.

The present invention is made in consideration of above-described problems. An object of the present invention is to provide a unit 30 for measuring optical property that can measure at least one of transmittance, reflectance and phase change in transmission or reflectance, more easily than before, without changing optical property of an optical system or moving a light receptor.

SUMMARY OF THE INVENTION (a) A unit 30 for measuring optical property in accordance with the present invention includes the following structure, as shown in FIGS. 1(A) and 1(B). FIGS. 1(A) and 1(B) explain the fundamental structure of the unit 30 for measuring optical property. FIG. 1(A) shows that a unit 30 for measuring optical property performs the first measurement (as described below) in the present invention. FIG. 1(B) shows that the unit 30 for measuring optical property performs the second measurement (as described below) in the present invention.

As to the unit 30 for measuring optical property, in the first measurement, an incident light beam is reflected in order by the first reflecting surface M1 through the fourth reflecting surface M4 as shown in FIG. 1(A), and in the second measurement, the incident light beam is reflected in order by the first reflecting surface M1, the fifth reflecting surface M5, the sixth reflecting surface M6 and the fourth reflecting surface M4 as shown in FIG. 1(B). The unit 30 for measuring optical property includes the reflecting surface M1 through the reflecting surface M6, a reflecting surface rotating device 31 that rotates the first and fourth reflecting surfaces M1 and M4, an object moving device 35 that inserts and extracts an object 33 (including a reference object) at a position between the second reflecting surface M2 and the third reflecting surface M3, or at a position between the fifth reflecting surface M5 and the sixth reflecting surface M6, and a reflection reflecting surface moving device 37 (as described later in detail).

The first reflecting surface M1 through the fourth reflecting surface M4 are arranged so that an optical path from the surface M1 through the surface M4 forms a shape of a letter "N" or a shape approximately like a letter "N", and so that the light L1 incident on the first reflecting surface M1 has the same axis as the exit light L2 that exits from the fourth reflecting surface M4. In the case of FIGS. 1(A) and 1(B), when these figures are seen from the back, a right shape of a letter "N" is read.

The first and fourth reflecting surfaces M1 and M4 are arranged so that the reflecting surfaces M1 and M4 are perpendicular to a plane containing the optical path of the letter "N".

A point O is an intersection that a line segment AD intersects an optical path BC: the line segment AD is a line segment that connects a point of incidence A, at which the incident light L1 impinges on the reflecting surface M1, with an exit point D at which the exit light L2 exits from the reflecting surface M4, the optical path BC is a path that connects a point B, at which light is reflected by the reflecting surface M2, with a point C at which light is reflected by the reflecting surface M3. Hereafter, the point O is called the optical center of the optical system. The second reflecting surface M2 forms the first ellipsoid of revolution having foci of the optical center O and the point of incidence A.

The third reflecting surface M3 forms the second ellipsoid of revolution having foci of the optical center O and the exit point D.

The fifth reflecting surface M5 makes light reflected from the first reflecting surface M1 parallel. The reflecting surface M5 is typically located so that the reflecting surface M5 makes light reflected from the reflecting surface M1 parallel or substantially parallel, and makes this paralleled light pass through the optical center O. The reflecting surface M5 forms the first parabolic mirror.

The sixth reflecting surface M6 converges light reflected from the fifth reflecting surface M5 onto the fourth reflecting surface M4. The reflecting surface M6 is typically located so that the reflecting surface M5 receives light reflected from the fifth reflecting surface M5 (the first parabola mirror) and converges this light onto the fourth reflecting surface M4. The reflecting surface M6 forms the second parabola mirror.

The reflecting surface rotating device 31 rotates the fourth reflecting surface M4 in conjunction with the rotation of the first reflecting surface M1 about an axis perpendicular to a plane containing the light path of the letter "N", i.e., an axis perpendicular to the page of FIGS. 1(A) and 1(B). Specifically, the rotating axis of the reflecting surface M1 is at the point of incidence A, and the rotating axis of the reflecting surface M4 is at the exit point D.

Rotating direction and the rotating amount of the first and fourth reflecting surfaces M1 and M4 are determined so that the incident light L1 and reflected light L2 have the same optical axis. Both of reflecting surfaces M1 and M2 could have the same rotating direction or reverse rotating direction. Both reflecting surfaces of M1 and M2 could have the same rotating amount or the different rotating amount. Although the reflecting surface M1 rotates along with the reflecting surface M2, both reflecting surfaces of M1 and M2 could rotate in a synchronized manner or not. Typically, the reflecting surfaces M1 and M2 rotate in a synchronized manner.

The object-moving device 35 chooses either of two states relating to the object 33. One state is a state that the object 33 is inserted between the reflecting surface M2 and the reflecting surface M3, or between the reflecting surface M5 and the reflecting surface M6, so that the measuring surface 33a contains the optical center O. Another state is a state that the object 33 is not inserted.

(b) The following explains the operation of the unit 30 for measuring optical property, referring to FIGS. 1(A) and 1(B).

The unit 30 for measuring optical property of the present invention performs the first measurement using the reflecting surfaces M1, M2, M3 and M4 as shown in FIG. 1(A), and the second measurement using the reflecting surfaces M1, M4, M5 and M6 as shown in FIG. 1(B).

①The first measurement, referring to FIG. 1(A), has the following operation. A line segment OH passes through the optical center O, and the line segment AD connects the point of incidence A with the exit point D. The line segment OH intersects connects the point of incidence A with the exit point D. The line segment OH intersects the line segment AD at the optical center O at an angle of 90 degrees. Let θ be an angle between the line segment OH and the optical path BC that runs from the reflecting surface M2 to the reflecting surface M3. When the measuring surface 33a of the object 33 is placed between the reflecting surface M2 and the reflecting surface M3 so that the measuring surface 33a contains the optical center O, this state of arrangement is called the first state. In the first state, the angle θ is an angle of incidence on the measuring surface 33a.

This angle of incidence on the object, the angle θ, can be changed arbitrarily, or continuously by rotating the reflecting surface M1. Because the unit 30 for measuring optical property rotates the first reflecting surface M1 about the axis described previously, and the second reflecting surface M2 has a shape of a predetermined ellipsoid of revolution. The following explains in further detail.

FIG. 2 is an explanatory drawing showing an optical system of the reflecting surface M1, the reflecting surface M2, which has a shape of an ellipsoid of revolution, and the object 33, which is inserted between the reflecting surface M2 and M3 as described above. In FIG. 2, although the reflecting surface M1 is actually the ellipsoid of revolution having a rotational axis x, for the purpose of simplicity, the reflecting surface M1 is treated as a two-dimensional ellipse. FIG. 2 is a figure that a portion of FIG. 1 is turned upside down.

Let $\phi$ be an angle that the reflecting surface rotating device 31 rotates the reflecting surface M1. This angle 100 has the following relation with the angle θ.

When $\psi$ is an angle between a light beam incident on the object 33 and the line segment AO, $\psi$ is equivalent to $\pi/2-\theta$. When e is eccentricity of the ellipse M2, and coordinates (-c, 0) and (c, 0) are foci of the ellipse M2, tangent of $\phi$ and tangent of $\psi$ are expressed by the following equations (1) and (2), respectively.

$$\tan \phi = y/(c+x) \qquad (1)$$

$$\tan \psi = y/(c-x) \qquad (2)$$

from equations (1) and (2), x and y are given $$x = c(\tan \phi - \tan \psi)/(\tan \phi + \tan \psi) \qquad (3)$$

$$y = 2c(\tan \phi \tan \psi)/(\tan \phi + \tan \psi) \qquad (4)$$

equations of ellipse and parameter are given $$(x/a)^2 + (y/b)^2 = 1 \qquad (5)$$

$$e^2 = (a^2+b^2)/a^2 \qquad (6)$$

$$c^2 = a^2+b^2 \qquad (7)$$

after equations (3) and (4) are substituted for equation (5), by using equations (6) and (7), tan $\phi$ is given $$\tan \psi = \{(1-e^2)^2 \tan \phi \pm \sqrt{2}*e(1-e^2) \tan^2\phi/(1-e^2)^2 - 4e^2 \tan \phi\} \qquad (8)$$

tan$\psi$=cot$\phi$ is used for equation (8)

$$\theta = \arctan\{(1-e^2)^2 - 4e^2 \tan \phi\}/\{(1-e^2)^2 \tan \phi \pm \sqrt{2}*e(1-e^2) \tan^2\phi\} \qquad (9)$$

Equation (9) shows that the angle θ of incidence on the measuring surface 33a is changed by angle $\phi$ that is the rotation angle of the reflecting surface M1. If angle $\phi$ is changed, the optical center O does not move and the length of the optical path ABO keeps constant. Because these facts come from the property of ellipse, and the point of incidence A and the optical center O are foci of the ellipse M2. Accordingly, if the reflecting surface M1 rotates, an optical path length, focal length and aberration of the optical system does not change. Therefore, optical properties of an object such as transmittance and reflectance can be measured without change of an optical path, a focal length and aberration of the optical system, with respect to the angle of incidence dependence.

Since the unit 30 for measuring optical property of the present invention can move the reflecting surface M4 in conjunction with the reflecting surface M1, the following operation is performed.

Referring to FIG. 1(A), when the reflecting surface M1 is rotated an angle φ, angle θ of incidence on the surface of the object 33 at the optical center O changes according to equation (9). The light passing through the optical center O reaches the reflecting surface M4 after reflected by the reflecting surface M3. Since the reflecting surface M4 is rotated an arbitrary angle by the reflecting surface rotating device 31 in conjunction with the reflecting surface M1, the exit light L2 can have the same optical axis as the light of incidence L1. This means that the light receptor (not shown) can be arranged after the reflecting surface M4 and can be placed on the extension of the line segment AD.

Variations of optical properties with respect to angle of incidence can be measured only by rotating the reflecting surfaces M1 and M4. Therefore, although a conventional apparatus has problems of exchanging and adjusting the optical system, it is not necessary for the present apparatus to exchange and adjust the exchanged optical system.

Since the unit 30 for measuring optical property of the present invention enables the object moving device 35 to insert and extract the object 33, it is possible to measure various optical properties such as transmittance, reflectance and phase change of in transmission and reflection.

In one example of the first measurement, transmittance and phase change in transmittance are measured in the following manner as shown in FIGS. 3(A) and 3(B).

Referring to FIGS. 3(A), the object moving device 35 firstly creates the state that the object is not inserted. Intensity of exit light L2 is measured, rotating reflecting surfaces M1 and M4 adequately by the reflecting surface rotating device 31. This operation is called the first operation. "Rotating the reflecting surfaces M1 and M4 adequately" means rotating the reflecting surface M1 so as to provide light to the object 33 at desired incident angle, and means rotating the reflecting surface M4 so that the exit light L2 has the same axis as the light of incidence L1.

The object moving device 35, then, creates the state that the object 33 is inserted at a position between the reflecting surfaces M2 and M3 so that the measuring surface 33a contains the optical center O (hereafter, this position is called "predetermined position"), as shown in FIG. 3(B). Intensity of the exit light L2 is measured, rotating the reflecting surfaces M1 and M4 adequately by the rotating device 31. This process is called the second process.

Although the first process is performed prior to the second process in the above explanation, the second process may be performed prior to the first process.

Phase change in transmission or transmittance of the object is measured based upon the intensity of light measured in the first process or the second process respectively. These processes are explained further in detail.

$$lr(\theta)=lo \times R1(\theta) \times R2(\theta) \times R3(\theta) \times R4(\theta) \qquad (10)$$

where lr(θ) is the amount of exit light L2 dependent on the incident angle θ that is obtained in the first process as shown in FIG. 3(A), lo is the amount of incidence, and R1(θ) to R4(θ) are reflectances at an angle θ.

The amount of exit light L2, which depends on the angle θ of incidence in the second process, referring to FIG. 3(B), is given by $$ls(\theta)=lo \times R1(\theta) \times R2(\theta) \times R3(\theta) \times R4(\theta) \times Rs(\theta) \qquad (11)$$

where Rs(θ) is a reflectance of the object 33 at an angle of θ.

As to factors of ls(θ) that are measured in the second process, factors other than the factor depending on the object 33, that is, factors other than Rs(θ) are the same as factors measured in the first process. Accordingly, transmittance Ts(θ), i.e., transmittance of the object that depends on an angle of incidence θ, is given by $$Ts(\theta)=ls(\theta)/lr(\theta) \qquad (12)$$

[SS19]With respect to phase change in transmittance, phase properties Φ1(θ) and Φ2(θ) are measured in the first and second processes respectively.

These phase properties Φ1(θ) and Φ2(θ) are measured in the following procedure. As to the light source and the light receptor, the light source unit 19 and the light receptor 21 as shown in FIG. 28 are used respectively. The light source unit 19 is arranged at the front of the reflecting surface M1, and the light receptor 21 is arranged behind the reflecting surface M4. Light emitted from the light source unit 19, i.e., the light of incidence L1, impinges on the unit 30 for measuring optical property. Intensity of light at the light receptor 21 is measured in the first and second processes. From these measured intensity of light and well-known calculation theory specific to ellipsometry, phase properties Φ1(θ) and Φ2(θ) are calculated. By using these calculated Φ1(θ) and Φ2(θ), phase change in transmittance of the object 33, i.e., Φs is given $$\Phi s=\Phi 2(\theta)-\Phi 1(\theta) \qquad (13)$$

② The second measurement, referring to FIG. 1(B), has the following operation.

The light of incidence L1 is reflected in order by the reflecting surface M1, the reflecting surface M5, the reflecting surface M6 and the reflecting surface M4. The optical path from the reflecting surface M1 to M4 is formed by rotating the reflecting surfaces M1 and M4 a predetermined angle, using the reflecting surface rotating device 31.

The reflecting surface M5 makes the light reflected from the reflecting surface M1 parallel and pass through the optical center O.

The reflecting surface M6 makes the light reflected from the reflecting surface M5 converge on the reflecting surface M4.

In this case, referring to FIG. 1(B), intensity of light is measured in two cases with respect to the object 33. When the object moving device 35 inserts the object 33 in the neighborhood of the optical center O between the reflecting surfaces M5 and M6, intensity of light can be measured by the light receptor (not shown), in the case that the optical system includes the object 33. When the object moving device 35 extracts the object 33, intensity of light can be measured in the case that the optical system excludes the object 33. Accordingly, the ratio of intensity of light for above-mentioned two cases, i.e., a transmittance for the object 33, is determined. Thus, in the second measurement, the unit 30 for measuring optical property can measure transmittance using parallel light. The unit 30 for measuring optical property also can measure dependence that transmittance depends on an angle of incidence, by rotating the object 33 at the optical center on the plane containing the optical path like the letter "N".

Measurement using parallel light means that transmittance can be measured by using measuring light having substantially zero NA (numerical aperture).

If reflectance is measured by using measuring light having some NA, especially large NA, light at the approximately center of luminous flux shows a different refractive index from that of light at the periphery of luminous flux. In the case of using large NA light, if the object is thin, it does not matter. But if the object is thick, light has a difference of traveling direction between at the center of and at the periphery of luminous flux. The thicker the object is, the larger the difference becomes. The difference of traveling direction results in the problem that a focus point in the optical system shifts, or that a part of light is not incident on the latter part of the optical system. Accordingly, measurement accuracy on transmittance of the thick object is not improved.

[SS21]However, since the unit 30 for measuring optical property of the present invention uses parallel measuring light, problems caused by a large NA can be solved or can be improved.

(c) It is preferable that the unit 30 for measuring optical property of the present invention has two states of the optical system. One state of the optical system is a state that the reflecting surfaces M3 and M4 produce an optical path like the "N" letter, and this state is called N state. Another state of the optical system is a state that the position of the reflecting surfaces M3 and M4 in the N state is turned 180 degrees about the line segment AD, and this state is called non-N state. The two states are created by driving a reflecting surface moving device 37, which is added to the unit 30 for measuring optical property.

The unit 30 for measuring optical property provided with the reflecting surface moving device 37 can measure reflectance (absolute reflectance) and phase change in reflection, varying an angle of incidence, as described in the following operation, referring to FIGS. 4(A) to 4(D). The object moving device 35 creates a state where the object is not inserted into the predetermined position of the optical system, and the reflecting surface moving device 37 creates the N state of the optical path as shown in FIG. 4(A). Then, the unit 30 for measuring optical property measures intensity of the exit light L2 such as the amount of light $lr(\theta)$, with the surface rotating device 31 rotating the reflecting surfaces M3 and M4 properly.

The object moving device 35 creates a state where the object 33 is inserted into the predetermined position, and the reflecting surface moving device 37 creates the non-N state as described above (FIG. 4(C)). Then, the unit 30 for measuring optical property measures intensity of the exit light L2 such as quantity of light $ls(\theta)$, with the surface rotating device 31 rotating the reflecting surfaces M1 and M4 properly, as shown in FIG. 4 (D). This operation is called the second operation.

Although the first operation is performed prior to the second operation in the above explanation, the second operation may be performed prior to the first operation.

When these first operation and second operation are performed, the reflecting surfaces M3 and M4 are moved by the reflecting surface moving device 37 so that the optical system of the N state or non-N state is created.

Thus, since the shape and the arrangement of the reflecting surfaces M3 and M4 of the present invention are defined as described above, moving the reflecting surfaces M3 and M4 does not change the optical path, a focal length and an aberration of the optical system, keeping the optical properties of the optical system unchanged.

Reflectance of the object 33 $Rs(\theta)$ is determined based upon the intensity of light measured in the first operation and second operation. Determining $Rs(\theta)$ has the same principle as determining reflectance as described above.

$$Rs(\theta)=ls(\theta)/lr(\theta) \qquad (14)$$

Phase change in reflection $\Phi s(\theta)$ is determined according to the method used in determining the phase change in transmittance.

$$\Phi s(\theta)=\Phi 1(\theta)-\Phi 2(\theta) \qquad (15)$$

where $\theta 2(\theta)$ is phase change in reflection (d) The unit 30 for measuring optical property having the reflecting surface moving device 37, in accordance with a preferred embodiment of the present invention, can measure the reflectance of the object relative to the reference object (i.e., relative reflectance) and the phase change in reflection of the object relative to the phase change in reflection of the reference object (hereafter, this phase change is called relative phase change in reflection), as shown in FIGS. 5(A) and 5(B).

The object moving device 37 creates the non-N state where the reflecting surfaces M3 and M4 are arranged into the non-N state of the optical system, and the object moving device 35 inserts the reference object 39 at the predetermined position between the reflecting surfaces M2 and M3 as shown in FIG. 5(A). This predetermined position is a position that the object 33 is inserted. Then, the unit 30 for measuring optical property measures the intensity of the exit light L2 such as the amount of light $lr(\theta)$, with the surface rotating device 31 rotating the reflecting surfaces M1 and M4 properly.

After that, the same operation described in FIG. 5(A), except for using the object 33 instead of the reference object 39, is performed. The unit 30 for measuring optical property measures the intensity of the exit light L2 such as the amount of light $ls(\theta)$.

Based upon the intensity of the exit light measured in the first and second operation, the unit 30 for measuring optical property measures the relative reflectance or relative phase change of the object 33, relative to the reference object 39. In this case, $lr(\theta)$ and $\Phi 1(\theta)$ of the reference object are used. Except for using these $lr(\theta)$ and $\Phi 1(\theta)$, a relative reflectance is determined by the equation (14), and relative phase change is determined by the equation (15).

In the case of the unit 30 for measuring optical property having a reflecting surface moving device 37a, the reflecting surface moving device 37a selectively creates either of the N state as shown in FIG. 6(A) or the non-N state as shown in FIG. 6(B), by moving only the reflecting surface M4. Instead of moving the reflecting surface M3, a reflecting surface M7 is placed at a position that the reflecting surface M3 should be placed.

In this case, the reflecting surface moving device 37a becomes simple because it does not need to move the reflecting surface M3. However, since difference between the reflecting surfaces M3 and M7 could affect the optical property of the system, it is preferable to use the reflecting surface M3 instead of the reflecting surface M7, and to move the reflecting surfaces M3 and M4 as described previously referring to FIG. 4.

(e) It is not always necessary to use the reflecting surfaces M2 and M3 that have the shape of ellipsoid of revolution in the following cases: when a diameter of a beam light is small; when a F number of the incident light is large; and when an optical path has a short distance because the total optical system is small. In these cases, it is possible to use a cylindrical ellipse instead of an ellipsoid of revolution. This cylindrical ellipse is a cylindrical ellipse that has the same ellipse curve as the ellipsoid of revolution and is perpendicular to a plane containing the "N" letter. It is also possible to use a spherical surface having a similar shape to the ellipsoid of revolution, or to use a cylinder having a similar shape to the ellipsoid of revolution. Since the diameter of the light beam is small, even if an angle of incidence is changed, the light reflected by the reflecting surface M1 is incident anywhere on the ellipse curve as depicted in FIG. 2. That is, the reflected light does not spread widely. Accordingly, the spherical or cylindrical shape of the reflecting surfaces M2 and M3 is equivalent to the shape of the ellipsoid of revolution. Furthermore, this spherical surface or cylindrical surface is easy to produce, and therefore, is inexpensive to produce.

(f) It is also possible to use a surface rotating device 41 (hereafter called "the second surface rotating device") as shown in FIG. 7, instead of the surface rotating device 31. This surface rotating device 41 rotates the reflecting surface M4 in conjunction with the reflecting surface M1 about the line segment AD that connects the point of incidence A with the exit point D.

When the surface rotating device 41 rotates the reflecting surface M1 an angle of $\alpha$ about the line segment AD, an angle of incidence $\theta$ on the surface 33$a$ is given.

$$\theta = \arccos \{\cos \theta_o \cos \alpha\} \quad (16)$$

where $\theta_0$ is an angle of incidence on the surface 33$a$ when an angle of $\alpha$ is 0 degree, referring to FIG. 8. In FIG. 8, N is a normal vector that is normal to the surface 33$a$, $S_0$ is a vector of light of incidence on the surface 33$a$ when an angle of $\alpha$ is 0 degree (i.e., an initial state of the reflecting surface M1), S is a vector of light of incidence on the reflecting surface M1 when the reflecting surface M1 is rotated $\alpha$ degrees about the line segment AD.

These three vectors are unit vectors. In FIG. 8, for the purpose of simplicity, the vector $S_0$ is set to have the same axis as the z axis, and the y axis is set so that the vector S moves in the y-z plane. In this case, the normal vector N is contained automatically in the x-z plane. Components of the vector N and the vector S are given.

$$N = (\sin \theta_0, 0, \cos \theta_0) \quad (17)$$

$$S = (0, \sin \alpha, \cos \alpha) \quad (18)$$

By using the inner product of above-mentioned vectors, the angle of incidence $\theta$ is given.

$$N \cdot S = |N||S_0| \cos \theta \quad (19)$$

Since $|N||S_0| = \cos\theta_0 \cos \alpha$, $|N|=1$, $|S_0|=1$, by substituting them to the equation (19), and by modifying the equation (19), the above-described equation (16) is lead.

When $\theta_0 = 10$ degrees, by rotating the reflecting surface M1 between 0 and 90 degrees, the angle of incidence $\theta$ can be changed between 10 and 90 degrees.

By using the second surface rotating device 41 instead of the surface rotating device 31, it is possible to design the unit 30 for measuring optical property differently, resulting in more flexibility in designing.

In the case of using the second surface rotating device 41, the following operations are performed as well as the case of using the reflecting surface rotating device 31. When the reflecting surface M1 is rotated, light reflected by the reflecting surface M1 and the reflecting surface M2 always passes through the optical center O. Because the reflecting surface M2 has the shape of the ellipsoid of revolution having foci of the point of incidence A and the optical center O. And the light path passing through the optical center O from the points A and B is unchanged when the reflecting surface M1 is rotated.

Furthermore, the second surface rotating device 41 can rotate the reflecting surface M4 in conjunction with the reflecting surface M1. The rotating direction of and the rotating amount of the reflecting surface M4 are adjustable so that the exit light L2 from the reflecting surface M4 has the same axis as that of the light incident on the reflecting surface M1.

Accordingly, in the case of arrangement using the second surface rotating device 41, optical properties such as light path, focal length and aberration of the optical system are kept unchanged.

In order to perform the second measurement using the second surface rotating device 41, that is, in order to measure transmittance with parallel light using the reflecting surfaces M1, M5, M6 and M4, the reflecting surfaces M5 and M6 are arranged so that light reflected from the reflecting surface M1 travels toward the reflecting surface M5 and the light reflected from the reflecting surface M6 converges toward the reflecting surface M4, when the reflecting surfaces M1 and M4 are located at a predetermined position.

(g) In this case of using the second surface rotating device 41, the same operation is performed, except for not using the surface rotating device 31. The unit 30 for measuring optical property measures optical properties such as transmittance, phase change in transmission, reflectance and phase change in refection of the object, as described below.

FIGS. 7(A) and 7(B) are explanatory drawings showing that the unit 30 for measuring optical property having the rotating device 41 measures transmittance and phase change in transmission. Referring to FIG. 7(A), the intensity of the exit light L2 is measured without inserting the object between the reflecting surfaces M2 and M3. Referring to FIG. 7(B), the intensity of the exit light L2 is measured, with the object being inserted at a predetermined position between the reflecting surfaces M2 and M3. Since determining transmittance and phase change in transmittance from these measured information is basically the same as the determination by using the rotating device 31, its explanation is omitted.

FIGS. 9(A) and 9(B) are explanatory drawings showing that the unit 30 for measuring optical property having the rotating device 41 measures absolute reflectance and phase change in reflection. Referring to FIG. 9(A), the intensity of the exit light L2 is measured without inserting the object between the reflecting surfaces M2 and M3. Referring to FIG. 9(B), the intensity of the exit light L2 is measured, with the object 33 being inserted at a predetermined position between the reflecting surfaces M2 and M3, and with the reflecting surfaces M3 and M4 being rotated 180 degrees about the line segment AD. Since determining absolute reflectance and phase change in reflection from these measured information is in principle the same as the determination by using the rotating device 31, its explanation is omitted.

FIGS. 10(A) and 10(B) are explanatory drawings showing that the unit 30 for measuring optical property having the rotating device 41 measures relative reflectance and phase change in reflection.

The surface rotating device 31 moves the reflecting surfaces M3 and M4 to the position of the non-N state of the optical path, not the N state. The reference object 39 is placed at a predetermined position as shown in FIG. 10(A), and the intensity of the exit light L2 is measured. Then, the object 33 is set instead of the reference object 39 at the predetermined position as shown in FIG. 10(B), and the intensity of the exit light L2 is measured. Since determining relative reflectance and relative phase change in reflection from these measured information is in principle the same as the determination by using the rotating device 31, its explanation is omitted.

(h) Also, in the case of using the second surface rotating device 41, as to the shape of the reflecting surfaces M2 and M3, it is possible to use the shape of a cylindrical ellipse instead of an ellipse of revolution, in the following cases: when a diameter of a beam light is small; when a F number of the incident light is large; and when an optical path has a short distance because the total optical system is small. These cases are described in detail as described below, referring to FIG. 11.

When the reflecting surface M1 is rotated, using the second rotating device 41 produces a locus of points on the reflecting surface M2, resulting in dots as shown in FIG. 11(A). The dots are located on the minor circumference of the spheroid, where ellipse has the smallest curvature as shown in FIG. 11(B), that is, dots are located on the circumference of the circle that is the spheroid's cross-section including minor axis of the ellipse, as shown in FIG. 11(C). Therefore, in the case that a diameter of light beam incident on the reflecting surface M2 is small, it is possible that the reflecting surfaces M2 and M3 has a shape of a cylinder having an axis of line segment AD, remaining the same function and advantage of the present invention.

DETAILED DESCRIPTION OF THE PREFERRED EMBODIMENT

Reference will now be made in detail to the preferred embodiments of the present invention, examples of which are illustrated in the accompanying drawings, wherein like reference number refers to like elements throughout, and explanations of like elements are omitted.

First Embodiment

Figure 12:
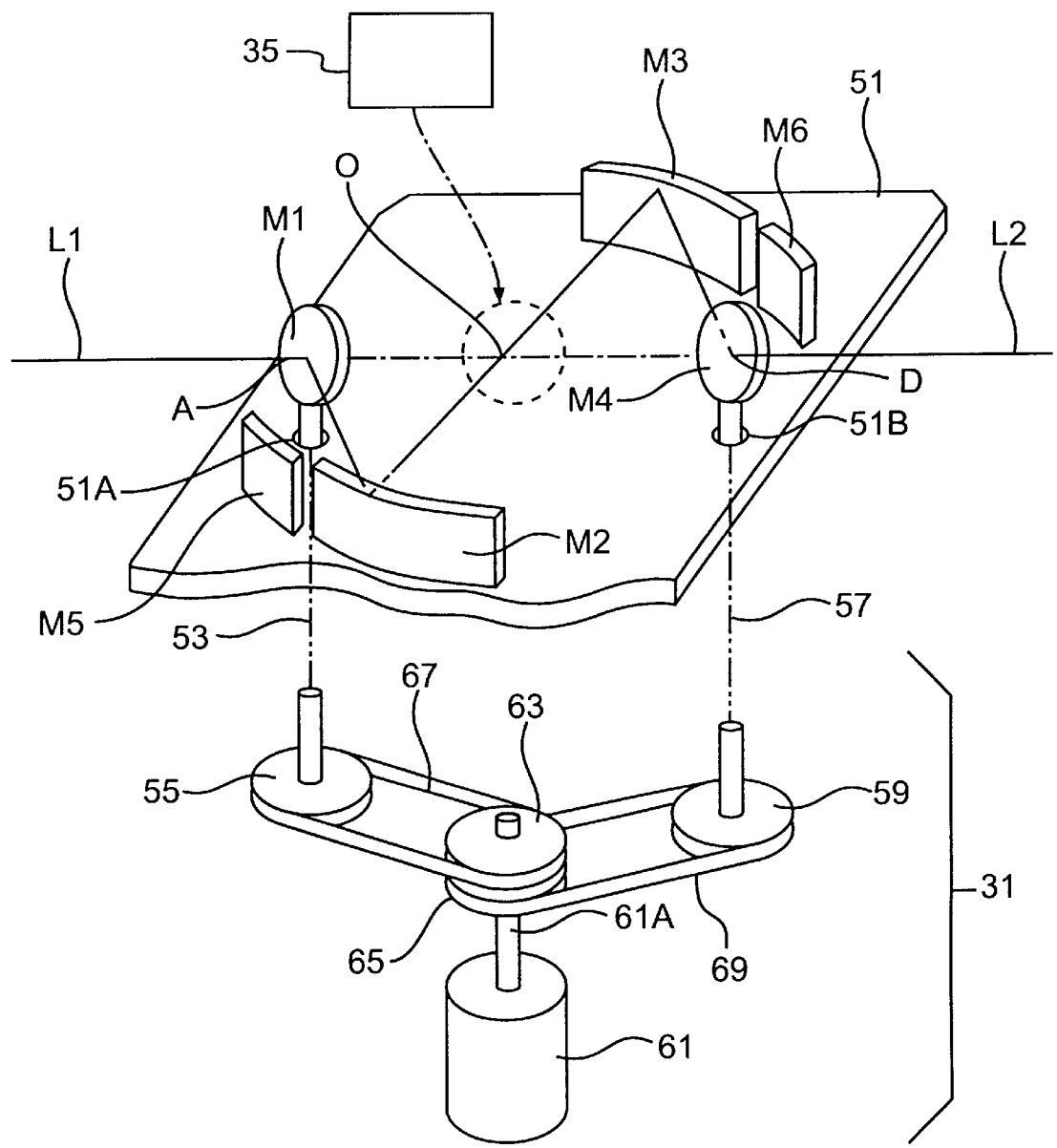
FIG. 12 is an explanatory drawing showing the first embodiment of the present invention.

FIG. 12 is a perspective view of the unit 30 for measuring optical property showing the first embodiment of the present invention.

The unit 30 for measuring optical property includes the first reflecting surface M1, the second reflecting surface M2, the third reflecting surface M3 and the fourth reflecting surface M4 in an optical system. These reflecting surfaces M1 to M4 are arranged on a base plate 51 so that an optical path extending the reflecting surface M1 to the reflecting surface M4 produces a shape like an "N" letter.

The fifth reflecting surface M5 and the sixth reflecting surface M6 are arranged at a predetermined position on the base plate 51 when the reflecting surfaces M1 and M4 are arranged at an arbitrary position and the second measurement (as described later) is performed. The predetermined position of the reflecting surface M5 is a position where the reflecting surface M5 can make light reflected from the reflecting surface M1 parallel and make this parallel light pass an optical center of the optical system. The predetermined position of the reflecting surface M6 is a position where the reflecting surface M6 can converge light reflected from the reflecting surface M5 on the reflecting surface M4.

The reflecting surfaces M5 and M6 can have a shape of parabolic mirror. When the reflecting surface M5, for example, has the shape of parabolic mirror, if the focus of the parabolic mirror is located at a point of incidence A on the reflecting surface M1 or near the point of incidence A, and the vertex of the parabolic mirror is located at a proper position, the reflecting surface M5 forms the fifth reflecting surface in the present invention. When the reflecting surface M6, for example, has the shape of parabolic mirror, if the focus of the parabolic mirror is located at a point D on the reflecting surface M4 or at a point near the point D, and the vertex of the parabolic mirror is located at a proper position, the reflecting surface M6 forms the sixth reflecting surface in the present invention.

The reflecting surfaces M1 and M4 are plane mirrors. The reflecting surface M2 has a shape of ellipsoid of revolution having foci of the point of incidence A and the optical center O. The reflecting surface M3 has a shape of ellipsoid of revolution having foci of the exit point D and the optical center O.

The reflecting surfaces M2 and M3 are fixed to the base plate 51. The reflecting surfaces M1 and M4 are not fixed to the base plate 51.

The reflecting surface M1 is connected to one end of a first rotating shaft 53. The first rotating shaft 53 passes through a through hole 51a of the base plate 51 and reaches a rear face of the base plate 51. The other end of the first rotating shaft 53 is connected to a first pulley 55.

The reflecting surface M4 is connected to one end of a second rotating shaft 57. The second rotating shaft 57 passes through a through hole 51b of the base plate 51 and reaches the rear face of the base plate 51. The other end of the second rotating shaft 57 is connected to a second pulley 59.

The unit 30 for measuring optical property has a motor 61, for example a stepping motor, as a rotating device. The third pulley 63 and the fourth pulley 65 are connected to a shaft 61 a of the motor 61.

The third pulley 63 is connected to the first pulley 55 with a belt 67. The fourth pulley 65 is connected to the second pulley 59 with a belt 69.

In the first embodiment, a reflecting surface rotational device 31 includes the rotating shafts 53 and 57, pulleys 55, 59, 63 and 61, and the motor 61.

The unit 30 for measuring optical property includes an object moving device 35. The object moving device 35 inserts an object or a reference object into a predetermined position and extracts from there. The object moving device 35 can be constructed by an arbitrary moving mechanism.

Rotation of the motor 61 is transferred to the reflecting surface M1 and M4 via pulleys and shafts. Accordingly, reflecting surfaces M1 and M4 can be rotated the same angle of degrees in the same direction.

If the reflecting surface M2 has the same ellipsoid of revolution as that of the reflecting surface M3, this allows a rotation angle of the reflecting surface M4 to be the same as that of the reflecting surface M1. If the reflecting surface M2 does not have the same ellipsoid of revolution as that of the reflecting surface M3, a driving condition of the reflecting surface M4 must be determined in consideration of the shape difference between reflecting surfaces M2 and M3.

Figure 3A:
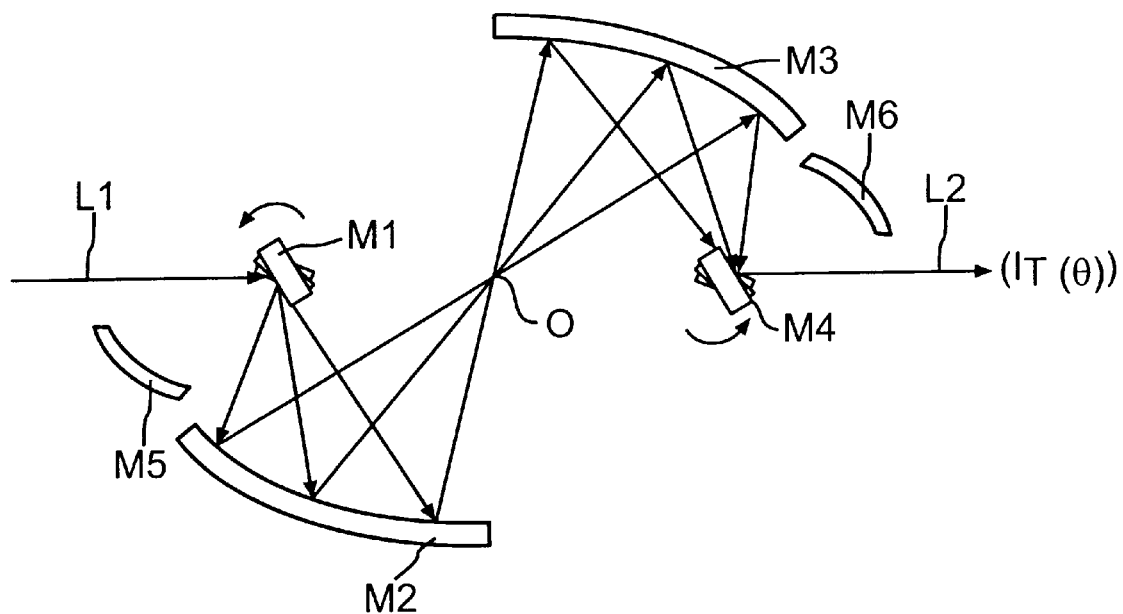
FIGS. 3A and 3B are explanatory drawings showing that the unit for measuring optical property measures transmittance and phase change in transmittance in accordance with a preferred embodiment of the present invention.
Figure 3B:
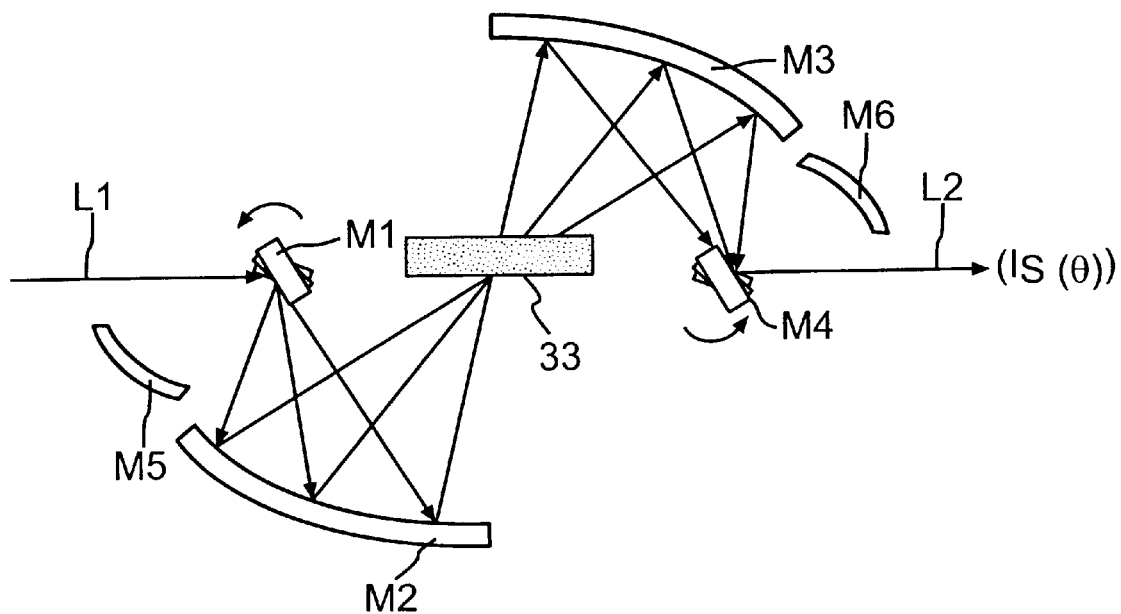

Referring to FIG. 12, the processes explained in FIGS. 3(A) and 3(B) are also possible.

Figure 1A:
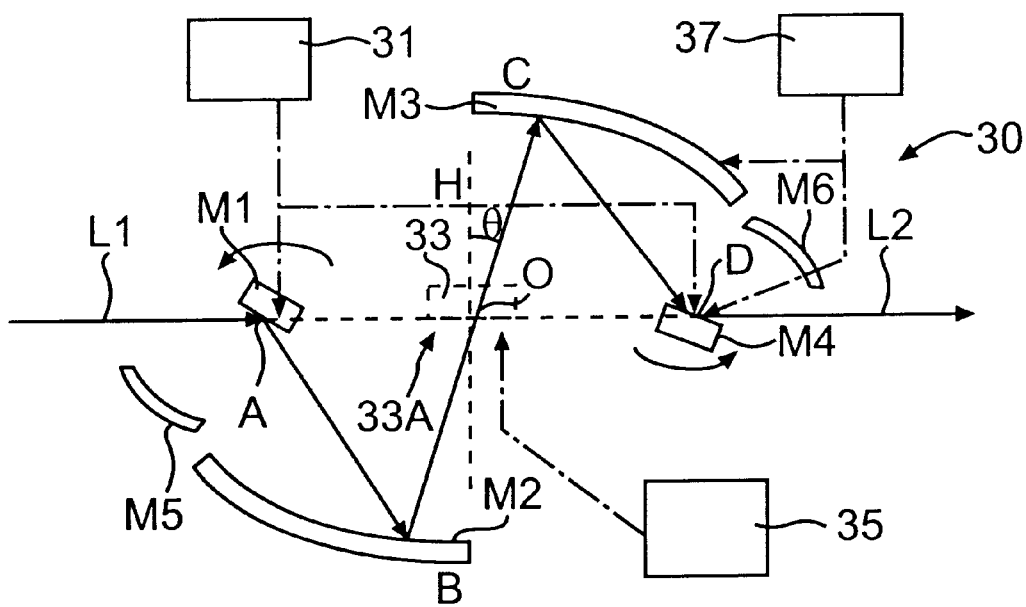
FIGS. 1A and 1B are explanatory drawings showing a unit for measuring optical property in accordance with a preferred embodiment of the present invention.
Figure 1B:
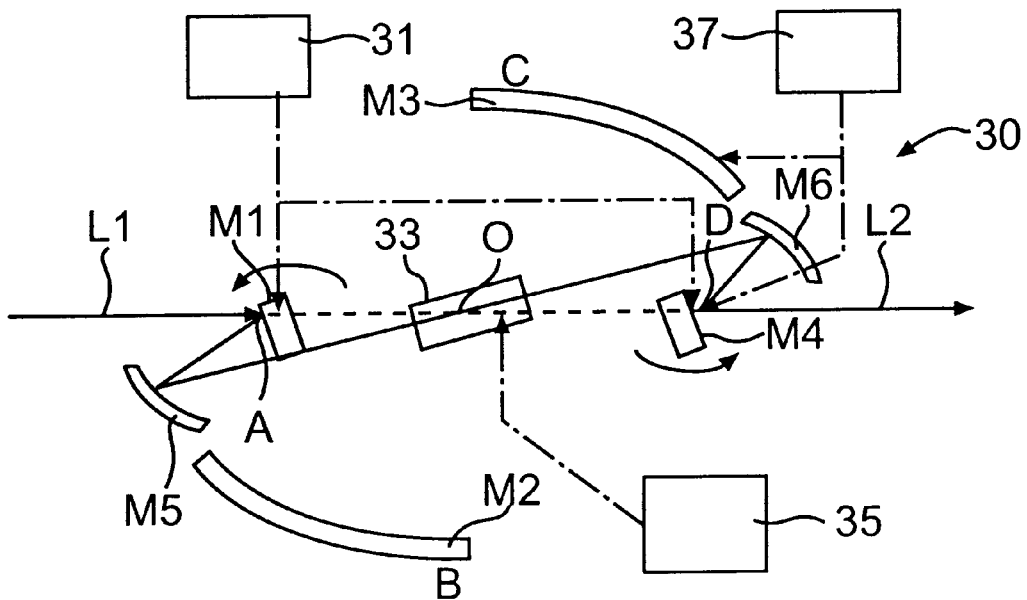
Figure 2:
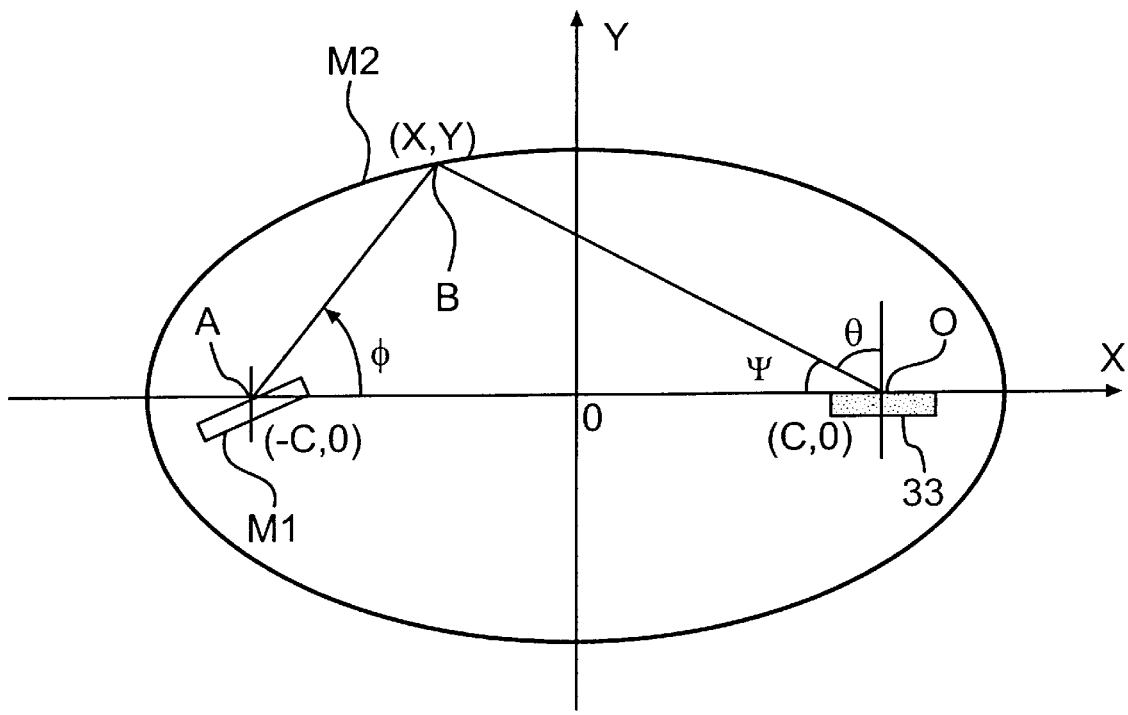
FIG. 2 is an explanatory drawing showing the state that an angle of incidence on an object is changeable in accordance with a preferred embodiment of the present invention.

Furthermore, referring to FIG. 12, by using the reflecting surfaces M1, M5, M6 and M4, the first measurement explained in FIG. 1(B), i.e., the measurement using parallel light is possible.

Second Embodiment

Figure 13:
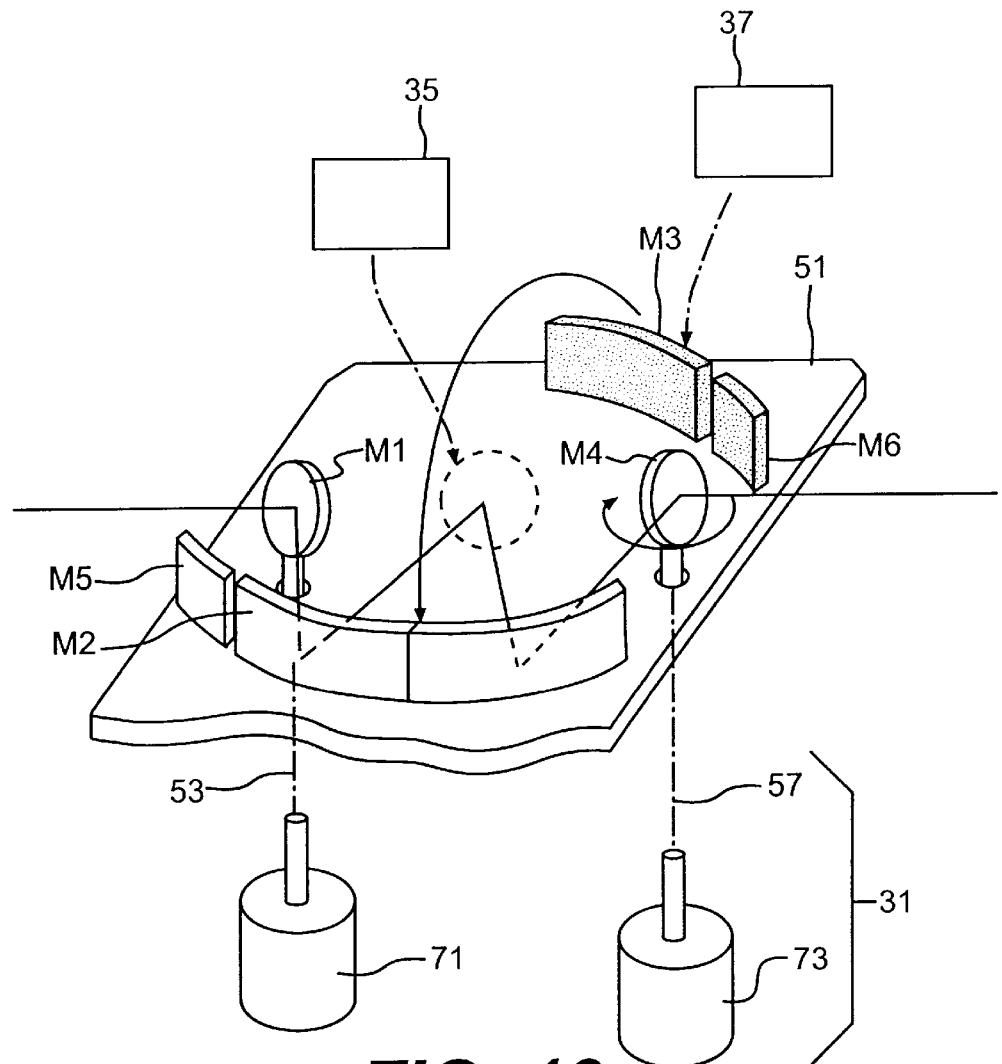
FIG. 13 is an explanatory drawing showing the second embodiment of the present invention.

FIG. 13 is a perspective view of the optical property measuring 30 unit showing the second embodiment of the present invention.

In the first embodiment, the reflecting surfaces M1 and M4 connect to the common motor 61 at the end of a transfer mechanism, but, in the second embodiment, the reflecting surface M1 connects to a motor 71, and the reflecting surface M4 connects to a motor 73. The motors 71, 73 and the rotating shafts 53, 57 form the reflecting surface rotating device 31.

In the second embodiment of the present invention, the independent drive of the two motors 71 and 73 enables the reflecting surfaces M1 and M4 to be controlled arbitrarily, regarding the rotation direction and the[SS33] amount of rotation. The combination of the motor 73 and the rotating shaft 57 forms a reflecting surface moving device 37 that rotates the surface M4 180° degrees about the line segment AD.

Although, in the first embodiment, the surface M3 is fixed to the base plate 51, the reflecting surface M3 of the second embodiment is not fixed to the base plate 51. And the reflecting surface M3 can be rotated 180° degrees about the line segment AD by the reflecting surface moving device 37.

The reflecting surface moving device 37 for moving the reflecting surface M3 can be formed by an arbitrary moving mechanism.

The use of the reflecting surface moving device 37 enables the operations as explained in FIGS. 4(A) to 4(D), since the reflecting surface moving device 37 rotates the reflecting surface M3 180° degrees about the line segment AD. By these operations, an absolute reflectance and phase change in reflection of the object can be measured.

Figure 5A:
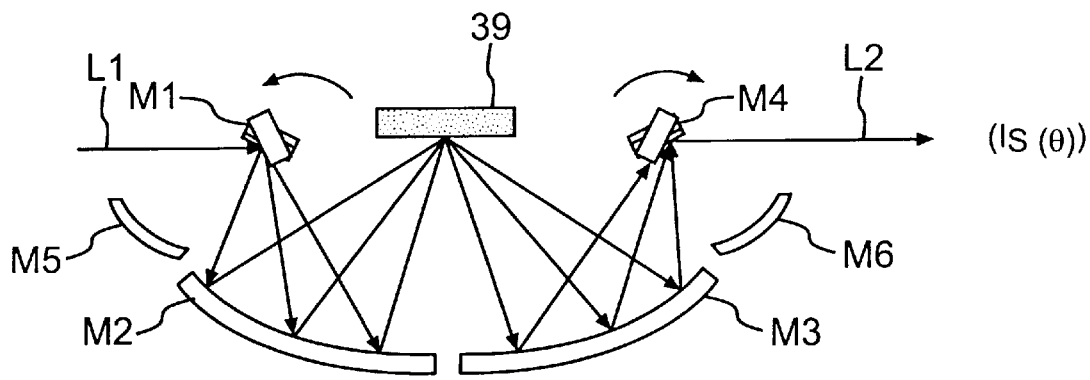
FIGS. 5A and 5B are explanatory drawings showing that the unit for measuring optical property measures relative reflectance and relative phase change in reflection in accordance with a preferred embodiment of the present invention.
Figure 5B:
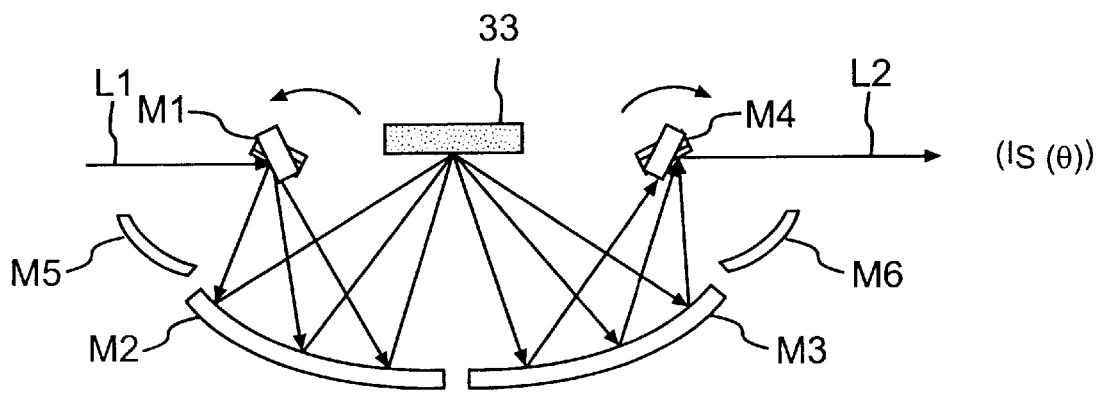
Figure 6A:
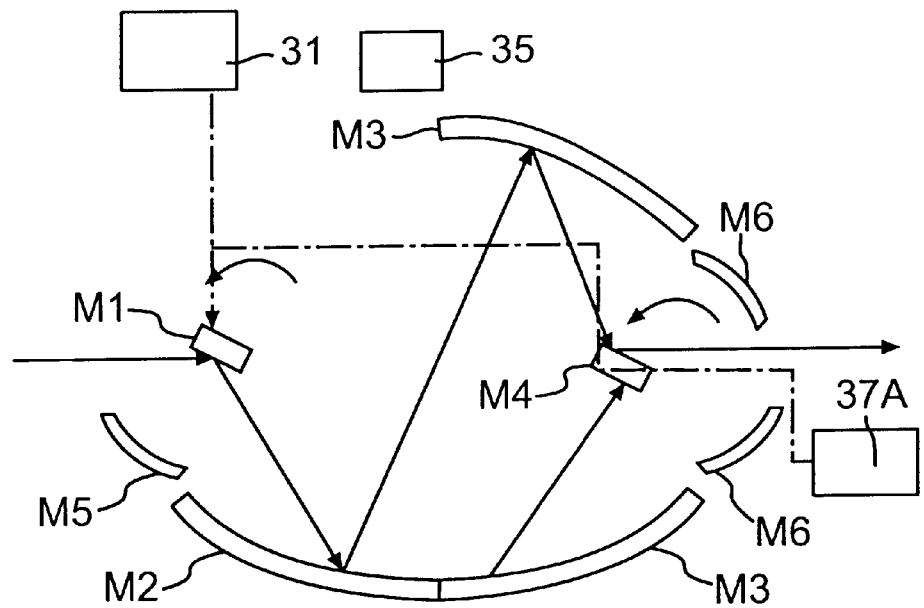
FIGS. 6A and 6B are explanatory drawings showing a modification of the unit for measuring optical property in accordance with a preferred embodiment of the present invention.
Figure 6B:
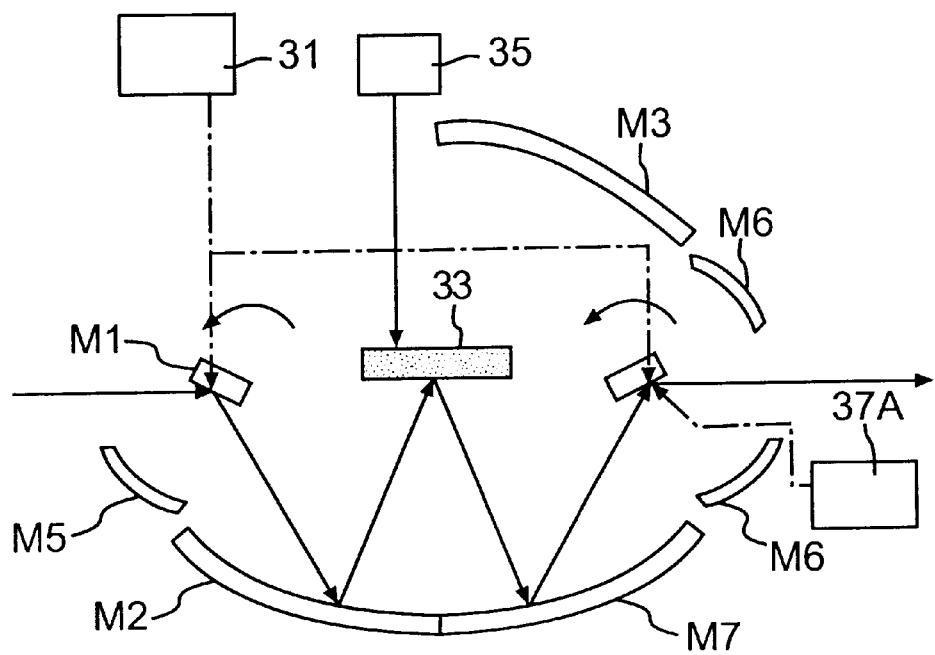
Figure 7A:
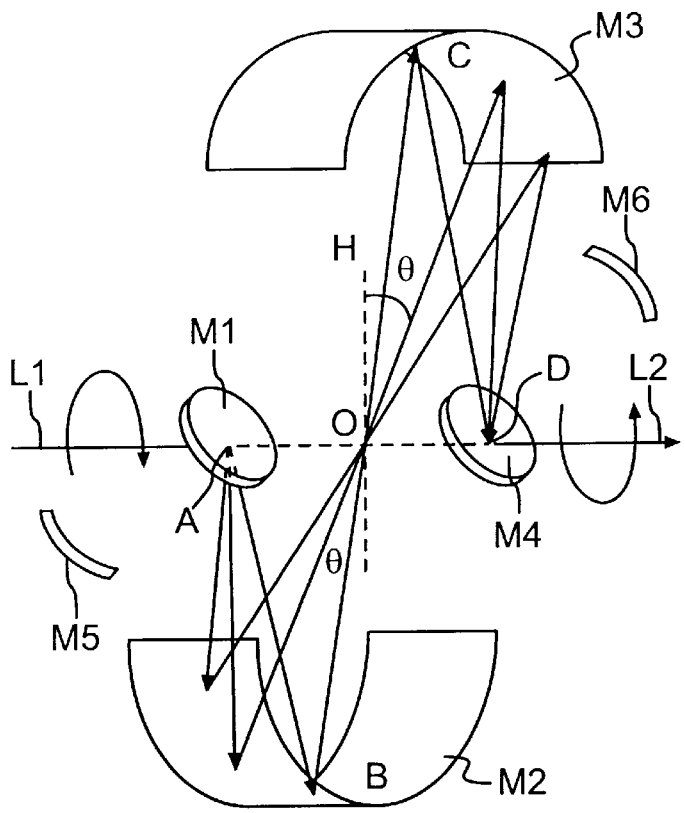
FIGS. 7A and 7B are explanatory drawings showing another modification of the unit for measuring optical property in accordance with a preferred embodiment of the present invention.
Figure 7B:
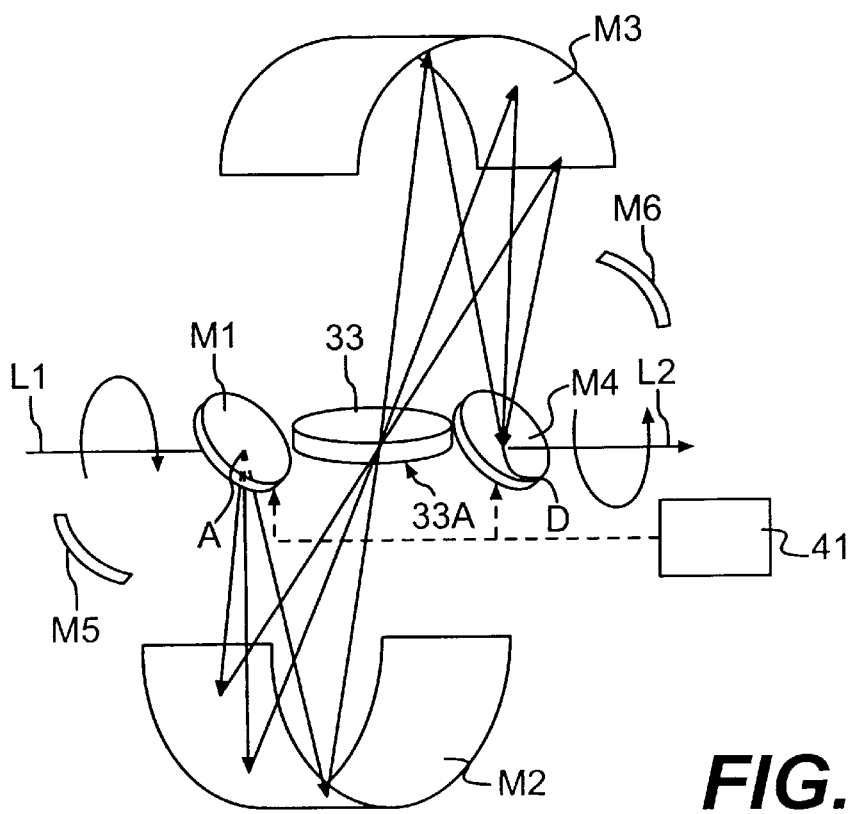
Figure 8:
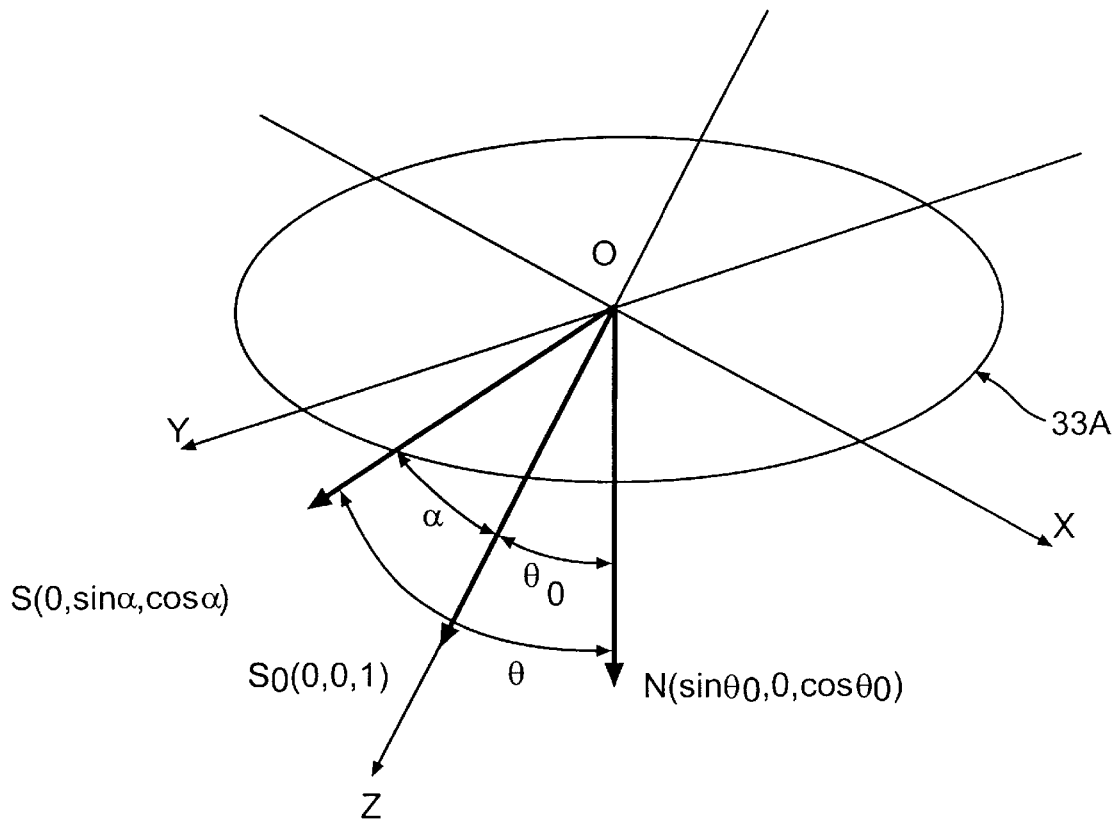
FIG. 8 is an explanatory drawing showing the second surface rotating device 41 in accordance with a preferred embodiment of the present invention.
Figure 9A:
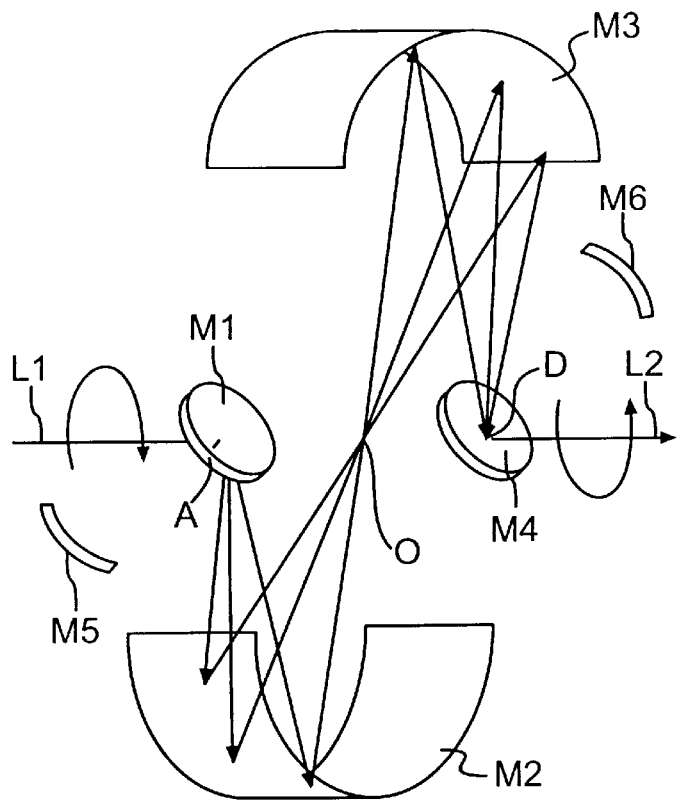
FIGS. 9A and 9B are explanatory drawings showing that the unit for measuring optical property having the second surface rotating device 41 measures absolute reflectance and phase change in reflection in accordance with a preferred embodiment of the present invention.
Figure 9B:
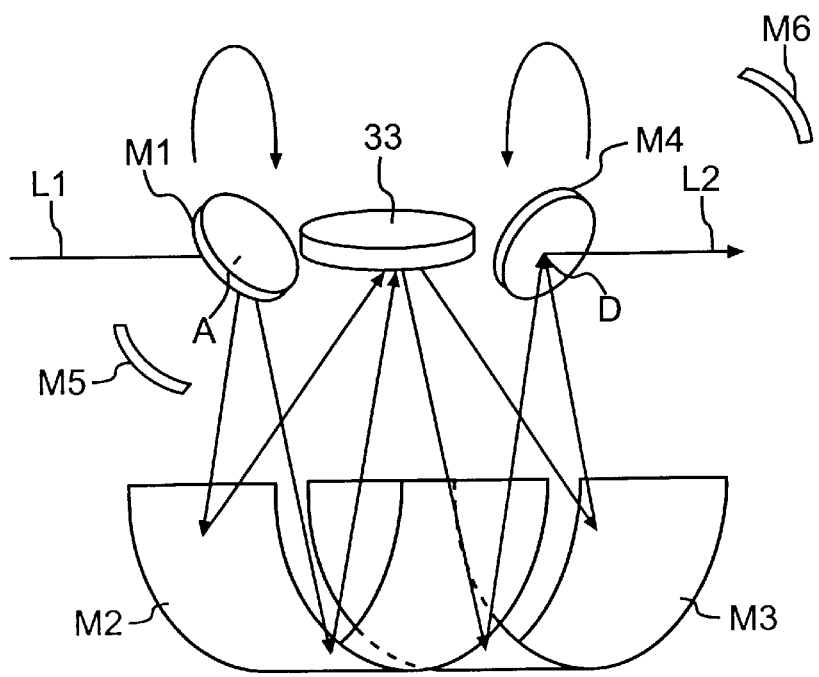
Figure 10A:
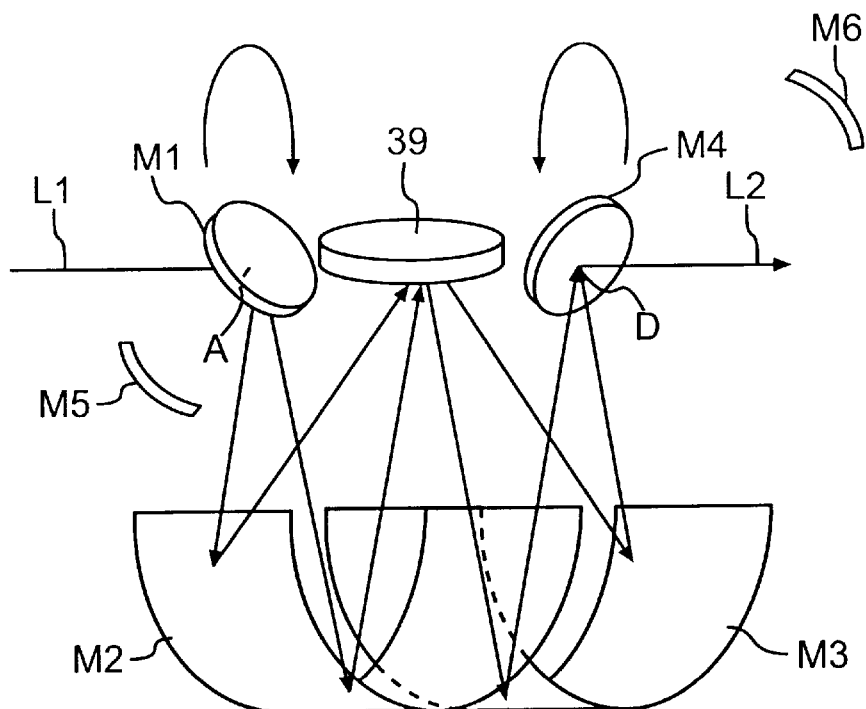
FIGS. 10A and 10B are explanatory drawings showing that the unit for measuring optical property having the second surface rotating device 41 measures relative reflectance and phase change in reflection in accordance with a preferred embodiment of the present invention.
Figure 10B:
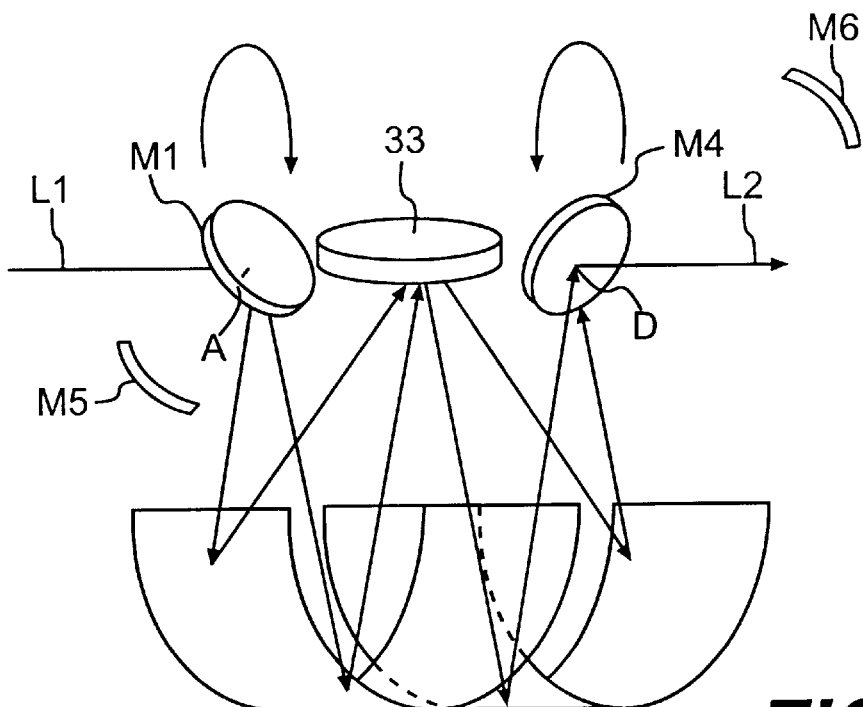
Figure 11A:
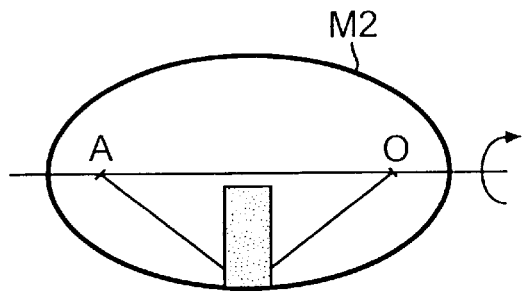
FIGS. 11A, 11B, 11C and 11D are explanatory drawings showing modifications of the second and third reflecting surfaces in accordance with a preferred embodiment of the present invention.
Figure 11B:
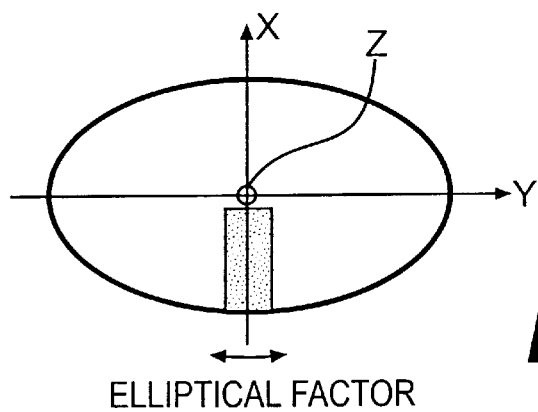
Figure 11C:
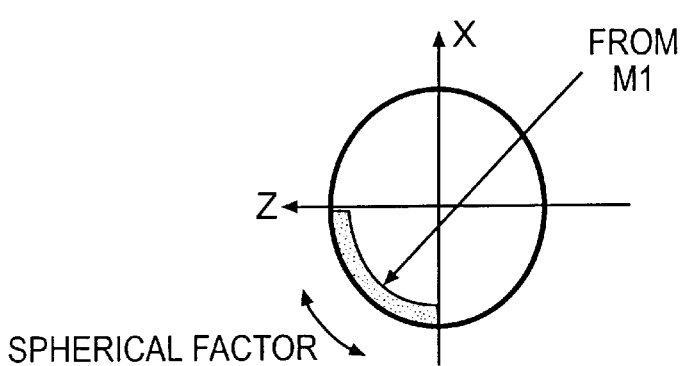
Figure 11D:
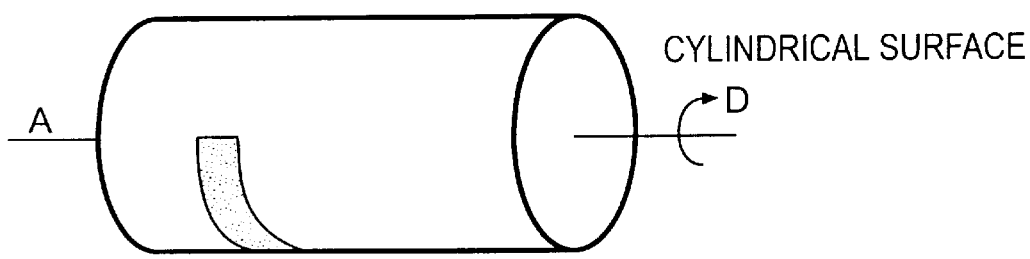

It is also possible to measure a relative reflectance and relative phase change in reflection, since operations as explained in FIGS. 5(A) and 5(B) is possible.

It is also possible to measure a transmittance as explained in FIGS. 3(A) and 3(B), and to measure a transmittance measured by using parallel light as explained in FIG. 1(B), as well as the first embodiment.

Thus, the second embodiment of the present invention can measure the following optical properties of the object: (1) an absolute reflectance and phase change in reflection; (2) a relative reflectance and relative phase change in reflection; (3) a transmittance and phase change in transmission; and (4) a transmittance measured by using parallel light.

Third Embodiment

Figure 14:
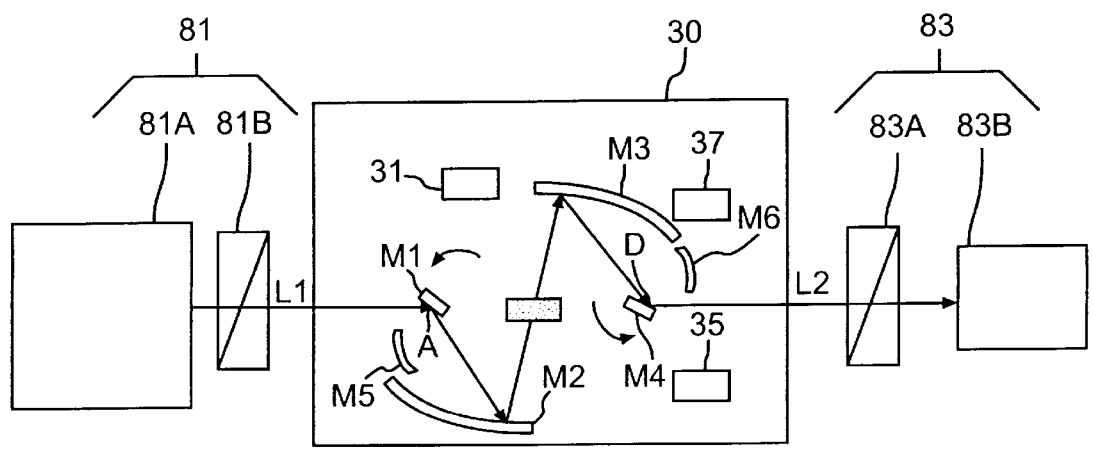
FIG. 14 is an explanatory drawing showing the third embodiment of the present invention.

FIG. 14 is an explanatory drawing showing one example that the unit 30 for measuring optical property of the present invention is applied to an ellipsometer.

This ellipsometer includes the unit 30 for measuring optical property, a light source unit 81 and a light receptor 83.

The light source 81 includes a light source 81a, such as a monochromater, capable of emitting light with an arbitrary wavelength, and a polarizer 81b. The light receptor 83 includes an analyzer 83a and a light-receiving element 83b.

Light emitted from the light source unit 81 is incident on the reflecting surface M1, as the incident light L1. The light receptor 83 is located behind the reflecting surface M4 and on the line segment AD.

Referring to FIG. 14, the ellipsometer having the following arrangement is realized. The ellipsometer includes the light source unit 81, the unit 30 for measuring optical property and the receptor 83 so that these three components are located on one line, without using goniostage. This feature is not realized in the past.

Fourth Embodiment

Figure 15:
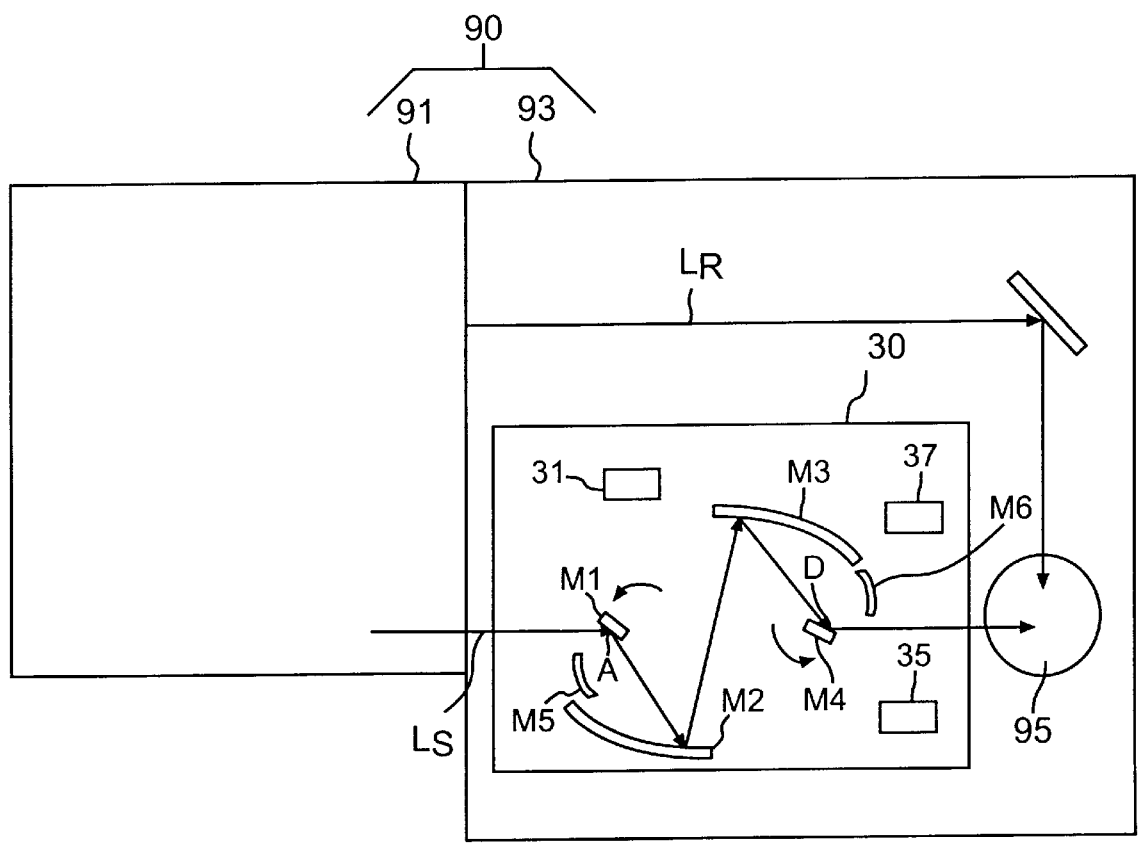
FIG. 15 is an explanatory drawing showing the fourth embodiment of the present invention.

FIG. 15 is an explanatory drawing showing one combination of the unit 30 for measuring optical property of the present invention and a commercial spectrophotometer 90.

The spectrophotometer includes the light source unit 91 and a measuring unit 93. The measuring unit 93 includes a reference optical path and a sample optical path therein. The light source unit 91 emits light alternatively to the reference optical path and the sample optical path. Hereafter, light traveling the reference optical path is called reference light Lr, and light traveling the sample optical path is called sample light Ls.

The unit 30 for measuring optical property is arranged on the sample optical path. The light receptor 95 receives the reference light Lr and sample light Ls alternatively.

Thus, according to the fourth embodiment of the present invention, the combination of the commercial spectrophotometer and the unit 30 for measuring optical property can measure the following optical properties of the object: (1) an absolute reflectance and phase change in reflection; (2) a relative reflectance and relative phase change in reflection; (3) a transmittance and phase change in transmission; and (4) a transmittance measured by using parallel light. Furthermore, it is not necessary to change or to adjust an optical system.

Fifth Embodiment

Figure 16:
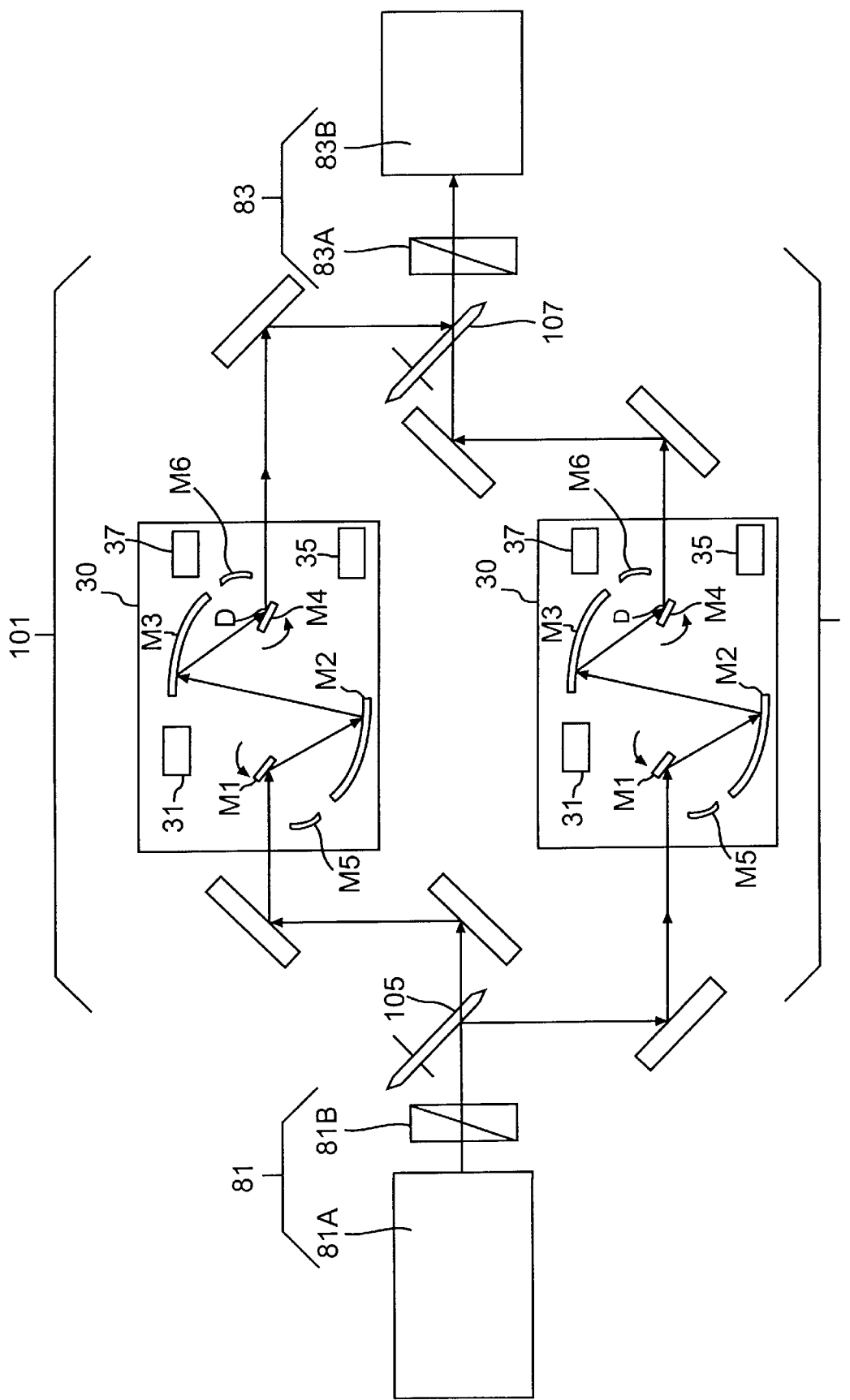
FIG. 16 is an explanatory drawing showing the fifth embodiment of the present invention.

FIG. 16 is an explanatory drawing showing one example that the unit 30 for measuring optical property of the present invention is applied to an ellipsometer, using double beam method.

This embodiment of the present invention includes a reference optical path 101 and a sample optical path 103 between the light source unit 81 and the light receptor 83. The unit 30 for measuring optical property is arranged on the reference optical path 101, and on the sample optical path 103, respectively.

A first chopper mirror 105 shakes the light, emitted from the light source unit 81, with time. One light travels the reference optical path 101, the other travels the sample optical path 103.

A second chopper mirror 107 is arranged in front of the light receptor 83. The second chopper mirror 107 selectively inputs one of the two light beams. One is the reference light that travels the reference optical path 101, the other is the sample light that travels the sample optical path 103.

According to the fifth embodiment of the present invention, the ellipsometer capable of measuring light with double beam method is realized. This leads to realization of a novel ellipsometer. That is, this ellipsometer has the feature of the unit 30 for measuring optical property and the advantage of double beam method that has high measurement accuracy.

Sixth Embodiment

Previously, the specification describes that the reflecting surfaces M2 and M3 has a shape of an ellipsoid of revolution, a predetermined spherical surface, cylindrical ellipse or cylinder (hereafter these shapes are called "the like of ellipsoid of revolution"). In the sixth embodiment, the reflecting surfaces M2 and M3 have a plain surface or a spherical surface even If the reflecting surfaces M2 and M3 are moved so that each of reflecting surfaces M2 and M3 corresponds to the like of ellipsoid of revolution, the reflecting surfaces M2 and M3 are included in the like of ellipse of revolution.

Figure 17:
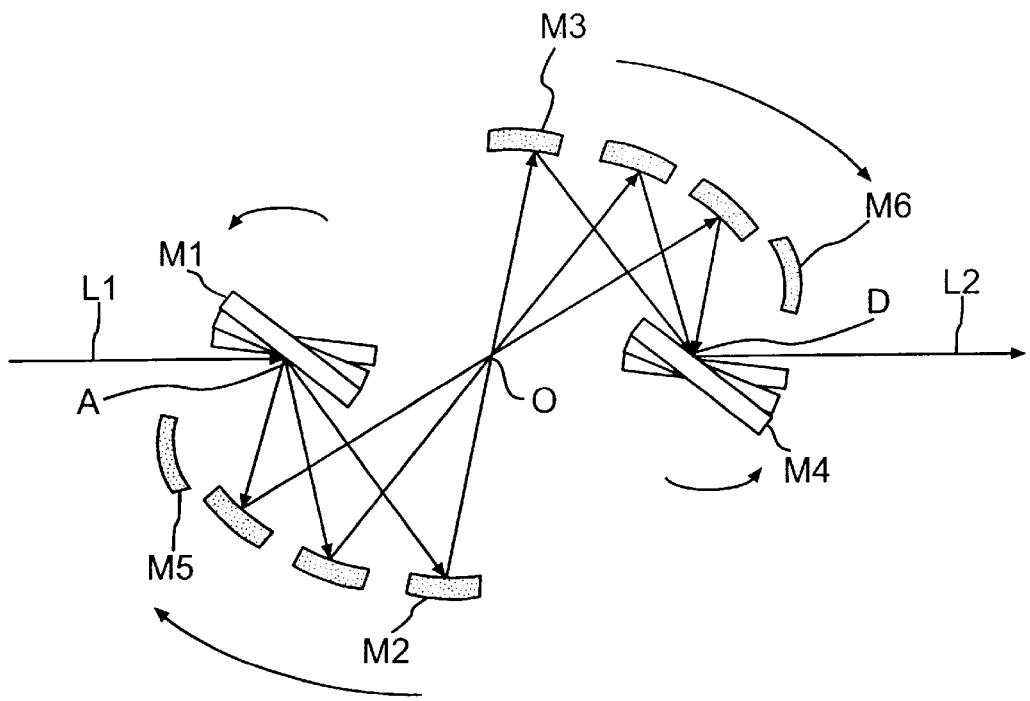
FIG. 17 is an explanatory drawing showing the sixth embodiment of the present invention.

Referring to FIG. 17, the reflecting surface M2 and M3 have a shape of a plain surface or a spherical surface. The reflecting surface M2 is moved to a position, synchronizing with the reflecting surface M1, such that the reflecting surface M2 can receive the light reflected from the reflecting surface M1 and the received light can pass through the optical center O of the optical system. The reflecting surface M3 is moved to a position, synchronizing with the reflecting surface M2, such that the reflecting surface M3 can receive the light reflected from the reflecting surface M2 and the received light can be incident of a point D on the reflecting surface M4.

In the sixth embodiment of the present invention, since the reflecting surfaces M2 and M3 are plain surface or spherical surface, the reflecting surfaces M2 and M3 can be small and inexpensive. But, a driving mechanism to follow the light beam is necessary.

EXAMPLE

The following examples explain resulting examples measured by the unit 30 for measuring optical property, along with other examples to be compared. The following facts regarding wavelength, angle of incidence and objects are not limited to only the following examples. The present invention is not limited to only these examples. Although measuring wavelength ranges from 175 nm to 250 nm in the following examples, wavelength ranging from 120 nm to 175 nm, wavelength over 250 nm including ultraviolet light, visible light and near-infrared light are also usable, because reflecting optical elements are used in this optical system.

Example 1

Example 1 indicates a case where an absolute transmittance is measured using parallel light. Referring to the optical system in FIG. 1(B), the intensity lr of the exit light L2 is measured without inserting the object into the measuring position. The wavelength of the incident light L1 is varied between 175 to 250 nm. The object 33, then, is inserted into the optical system, and the intensity ls of the exit light L2 is measured as well as the intensity lr. The object 33 is a rectangular parallelepiped having a length of 20 mm, a width of 20 mm and a thickness of 50 mm, made of quartz. The feature of this object 33 is its large thickness such as 50 mm.

Figure 18:
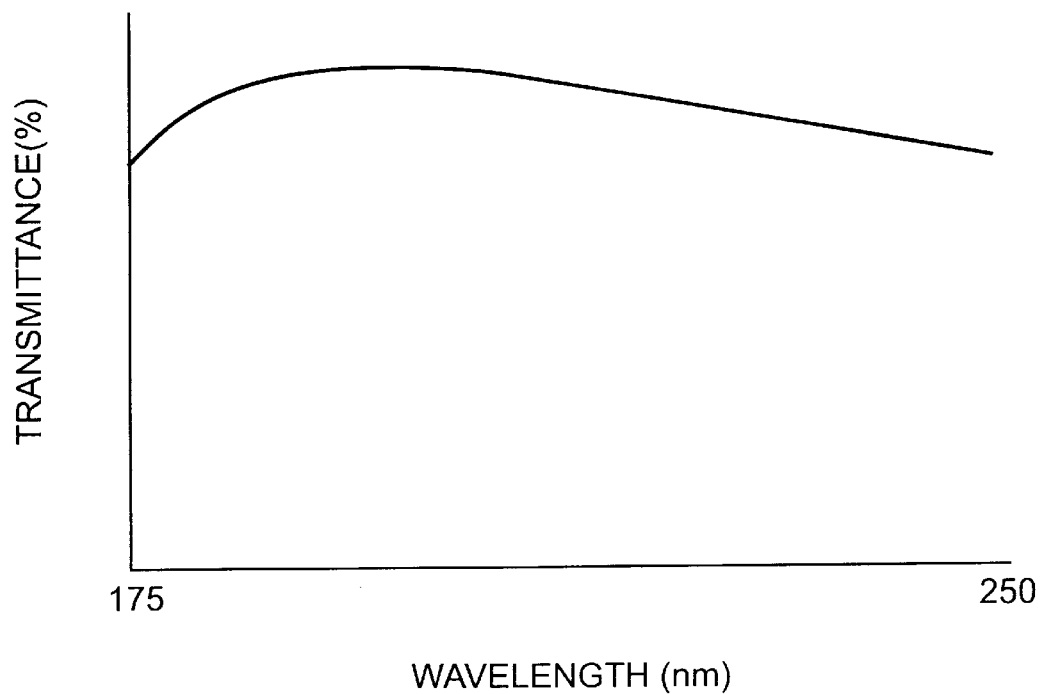
FIG. 18 is an explanatory drawing showing a measurement result achieved in the first embodiment of the present invention.

From these measured ls and lr, transmittance Ts for each wavelength is calculated by Ts=ls/lr. FIG. 18 is a graph of the determined transmittance Ts. The horizontal axis of the graph is wavelength, the vertical axis is the transmittance. Thus, even if a thickness of an object is large, transmittance can be measured.

Comparing Example 1

By using the optical system as shown in FIGS. 3(A) and 3(B) and performing the corresponding operation, transmittance is determined, wherein the reflecting surfaces M1 to M4 are used.

Transmittance (not shown) determined in this comparing example 1 is smaller than the transmittance determined in the example 1. Because the unparalleled incident light L1 spreads in all directions in the object when the object is inserted into the optical system and ls is measured, and the cross section of the luminous flux exiting from the object becomes larger than the area of the light-receiving element (not shown).

Thus, according to example 1 and comparing example 1, the unit 30 for measuring optical property can accurately determine the transmittance of an object having large thickness.

Example 2

In example 2, an absolute transmittance of an optical member is measured. The optical member, which has a diameter of 20 mm and a thickness of 2 mm, has thin film on the quartz base plate. Firstly, the intensity lr of the exit light is measured using the optical system as shown in FIG. 3(B), in a state where the object is not inserted into the optical system. The incident light L1 is p-polarized light having a wavelength of 190 nm, and varies its angle of incidence on the thin film between 5 to 30 degrees. Then, the object, i.e., the quartz base plate with thin film, is inserted into the optical system, and the intensity ls of the exit light is measured as well as lr. From these measured ls and lr, the transmittance ls/lr is calculated.

Figure 19:
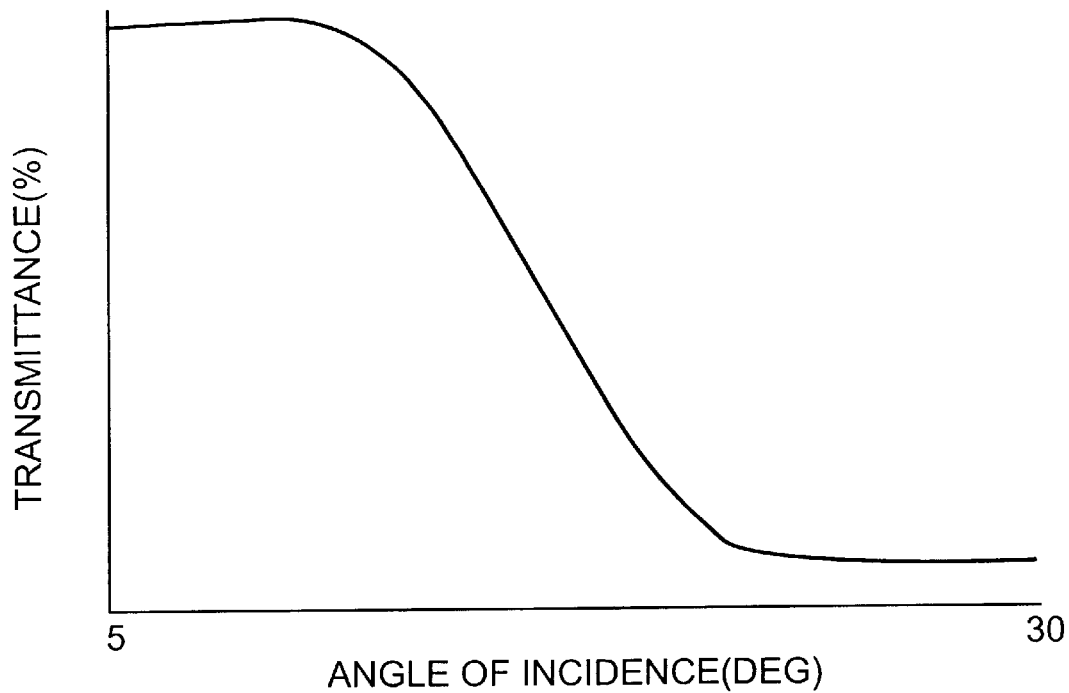
FIG. 19 is an explanatory drawing showing a measurement result achieved in the second embodiment of the present invention.

FIG. 19 is a graph of the determined transmittance Ts. The horizontal axis of the graph is angle of incidence (degree), the vertical axis is the transmittance. Thus, according to the present invention, angle-of-incidence dependence of phase change in transmission can be determined.

Example 3

In example 3, an absolute transmittance of an optical member is measured. The optical member, which has a diameter of 20 mm and a thickness of 2 mm, has anti-reflection film on a quartz base plate. Firstly, the intensity lr of the exit light is measured using the optical system as shown in FIG. 3(B), in a state where the object is not inserted into the optical system. The incident light L1 is p-polarized light having a wavelength of 175 to 250 nm, and is incident on the anti-reflection film at an angle of incidence of 30 degrees. Then, the object, i.e., the quartz base plate with anti-reflection film, is inserted into the optical system, and the intensity ls of the exit light is measured as well as lr. From these measured ls and lr, the transmittance Ts=ls/lr is calculated.

Figure 20:
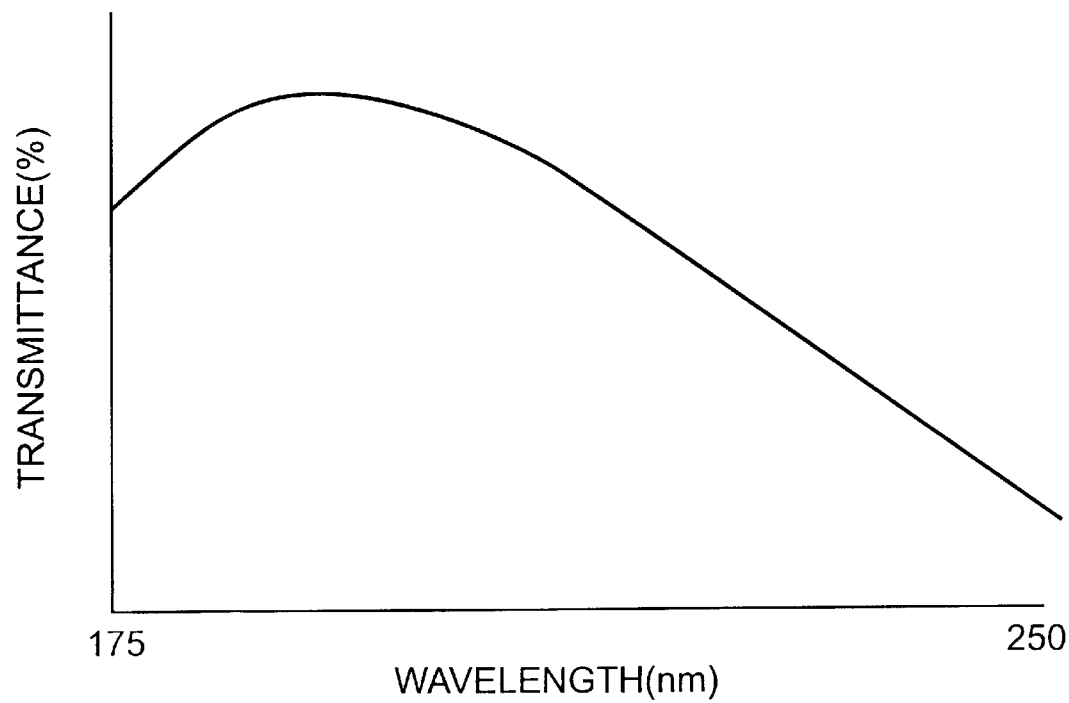
FIG. 20 is an explanatory drawing showing a measurement result achieved in the third embodiment of the present invention.

FIG. 20 is a graph of the above-mentioned transmittance Ts. The horizontal axis of the graph is angle of incidence (degree), and the vertical axis is transmittance. Thus, according to the present invention, angle-of-incidence dependence of phase change in transmission can be determined.

Example 4

In example 4, phase change in transmission of thin film is measured. The thin film is formed on a quartz base plate that has a diameter of 20 mm and a thickness of 2 mm. Firstly, phase property $\phi r$ ($\theta$) is measured using the optical system as shown in FIG. 3(B), in a state where the quartz base plate is inserted into the optical system. The incident light L1 has a wavelength of 190 nm, and is incident on the thin film at an angle of incidence of 30, 50 and 60 degrees. Then, the object, i.e., the quartz base plate with thin film is inserted into the optical system as shown in FIG. 3(B), and phase property $\phi s$ ($\theta$) is measured as well as the phase property $\phi r$ ($\theta$). From these measured $\phi r$ ($\theta$) and $\phi s$ ($\theta$), the phase change in transmission of thin film $\phi S$ ($\theta$)–$\phi r$ ($\theta$) is calculated.

Thus, according to the fourth example of the present invention, the phase change in transmission of thin film can be determined.

Example 5

Figure 4A:
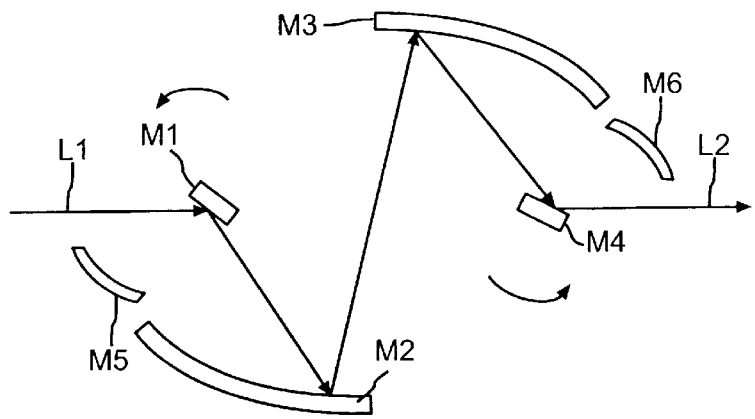
FIGS. 4A, 4B, 4C, and 4D are explanatory drawings showing that the unit for measuring optical property measures absolute reflectance and phase change in reflection in accordance with a preferred embodiment of the present invention.
Figure 4B:
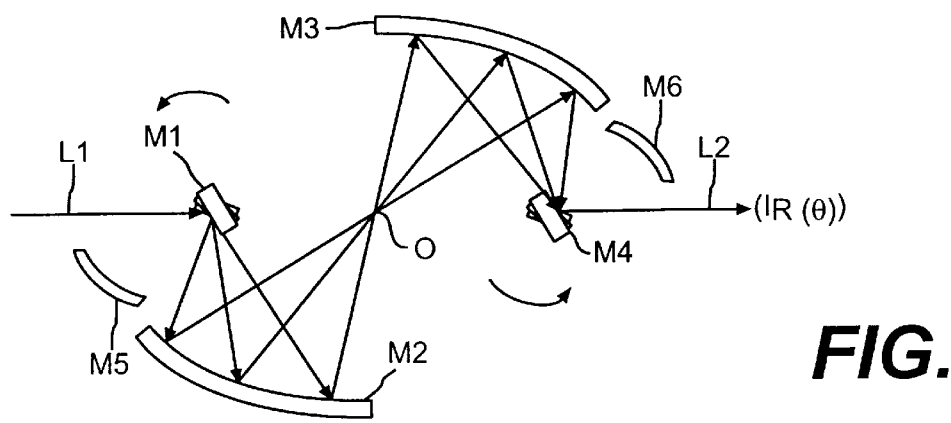
Figure 4C:
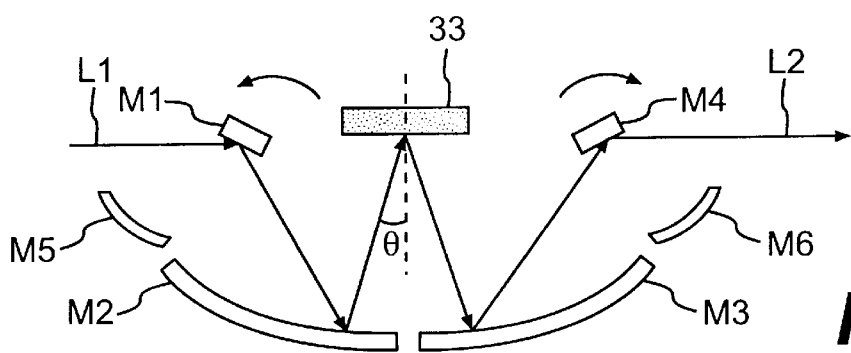
Figure 4D:
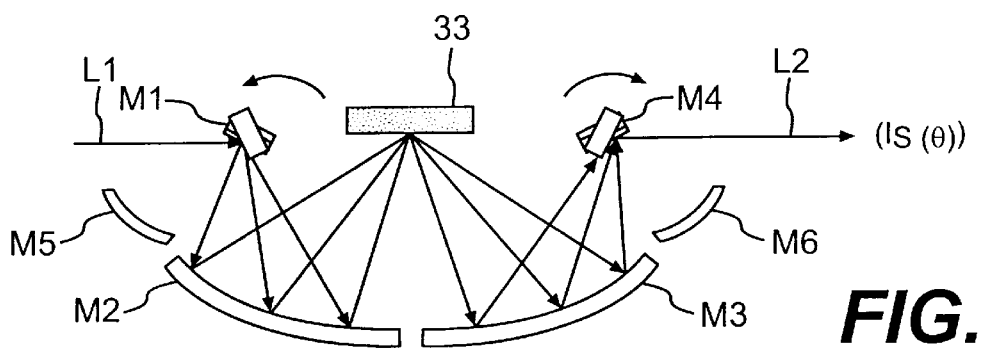
Figure 21:
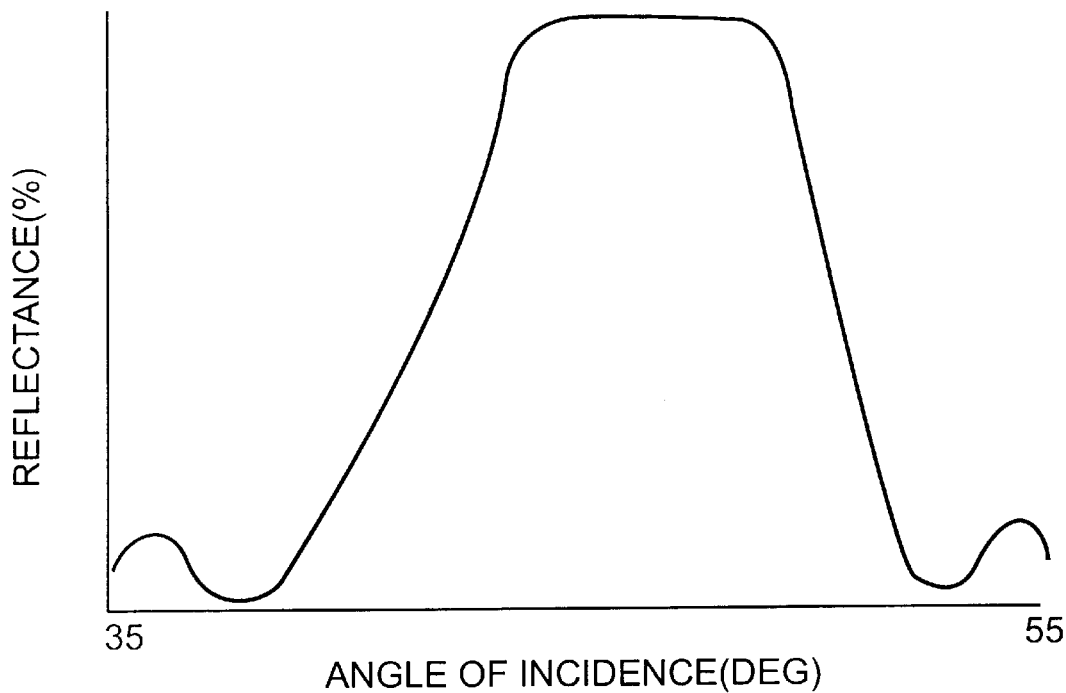
FIG. 21 is an explanatory drawing showing a measurement result achieved in the fifth embodiment of the present invention.

In example 5, an absolute reflectance of a mirror (depending upon angle-of-incidence) is measured. The mirror is formed on a quartz base plate that has a diameter of 20 mm and a thickness of 2 mm. Firstly, the intensity lr of the exit light is measured using the optical system as shown in FIGS. 4(A) and 4(B), in a state where the object is not inserted into the optical system. The incident light L1 is p polarized light having a wavelength of 190 nm, and is incident on the mirror at an angle of incidence between 35 and 55 degrees. Then, the reflecting surfaces M3 and M4 are moved by the reflecting surface moving device 37 as shown in FIGS. 4(C) and 4(D). And after the object, i.e., the quartz base plate with the mirror, is inserted into the optical system, the intensity ls of the exit light is measured as well as the intensity lr of the exit light. From these measured lr and ls, the reflectance ls/lr is calculated. FIG. 21 is a graph of the above-mentioned reflectance. The horizontal axis of the graph is angle of incidence (degree), and the vertical axis is reflectance. Thus, according to the present invention, angle-of-incidence dependence of absolute reflectance of a mirror can be determined.

Example 6

Figure 22:
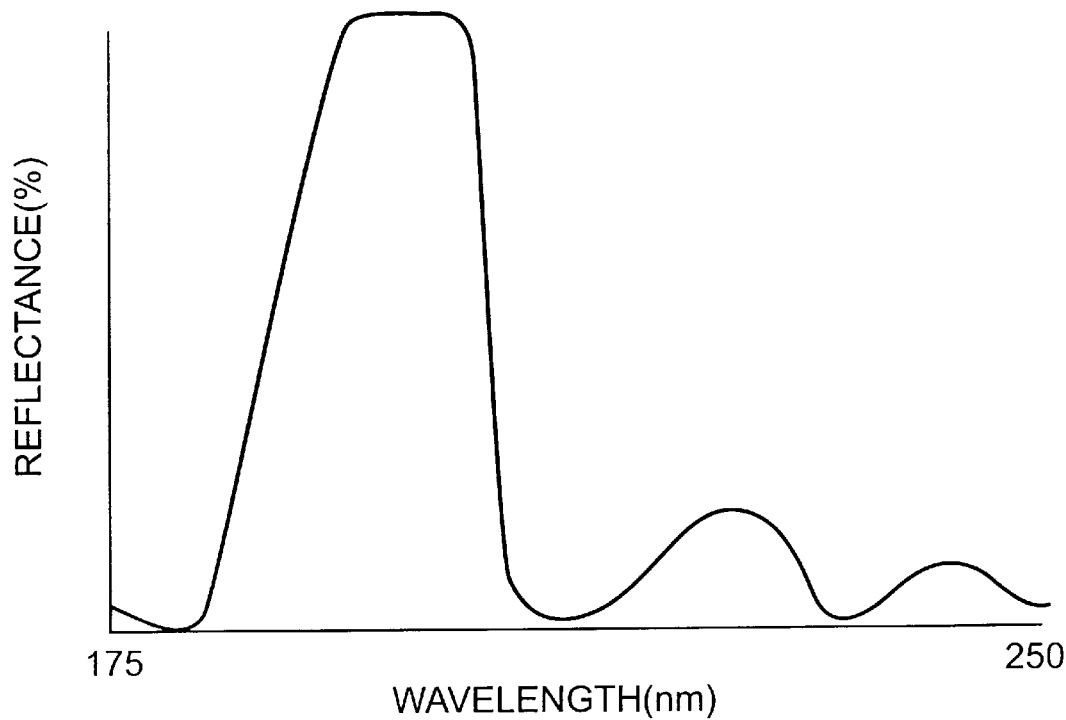
FIG. 22 is an explanatory drawing showing a measurement result achieved in the sixth embodiment of the present invention.

In example 6, absolute reflectance of a mirror (depending upon wavelength) is measured. The mirror is formed on a quartz base plate that has a diameter of 20 mm and a thickness of 2 mm. Firstly, the intensity lr of the exit light is measured using the optical system as shown in FIGS. 4(A) and 4(B), in a state where the object is not inserted into the optical system. The incident light L1 is p-polarized light of which wavelength ranges from 175 to 250 nm, and is incident on the mirror at an angle of incidence of 45 degrees. Then, the reflecting surfaces M3 and M4 are moved by the reflecting surface moving device 37 as shown in FIGS. 4(C) and 4(D). And after the object, i.e., the quartz base plate with mirror, is inserted into the optical system, the intensity ls of the exit light is measured as well as the intensity lr of the exit light. From these measured lr and ls, the reflectance ls/lr is calculated. FIG. 22 is a graph of the above-mentioned reflectance. The horizontal axis of the graph is wavelength, and the vertical axis is reflectance. Thus, according to the present invention, wavelength dependence of absolute reflectance of a mirror can be determined.

Example 7

Figure 23:
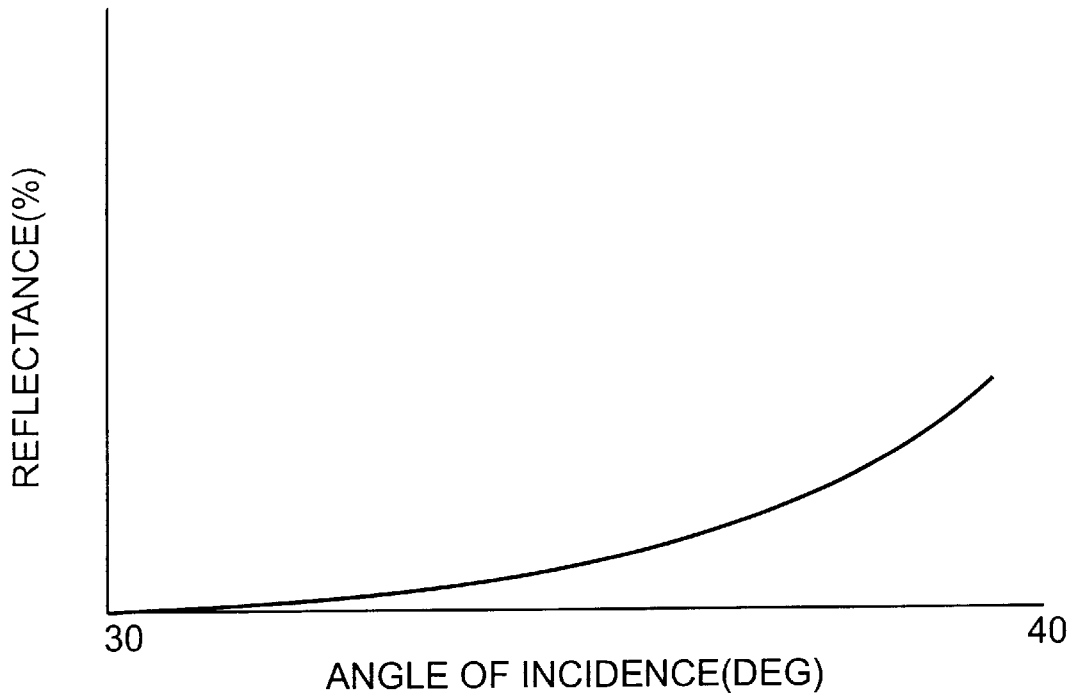
FIG. 23 is an explanatory drawing showing a measurement result achieved in the seventh embodiment of the present invention.

In example 7, relative reflectance of anti-reflection film is measured. The anti-reflection film is formed on a quartz base plate that has a diameter of 20 mm and a thickness of 2 mm. Firstly, the intensity lr of the exit light is measured using the optical system as shown in FIG. 5(A), in a state where the object 39, i.e., the quartz base plate without the anti-reflection film, is inserted into the optical system. The incident light L1 is p-polarized light having a wavelength of 190 nm, and an angle of incidence on the quartz base plate is changed between 20 and 40 degrees. Then, the intensity ls of the exit light is measured as shown in FIG. 5(B), in a state where the object 33, i.e., the quartz base plate with the anti-reflection film, is inserted into the optical system. From these measured lr and ls, the reflectance ls/lr is calculated. FIG. 23 is a graph of this reflectance. The horizontal axis of the graph is angle of incidence, and the vertical axis is reflectance. Thus, according to the present invention, angle-of-incidence dependence of relative reflectance of anti-reflection film can be determined.

Example 8

Figure 24:
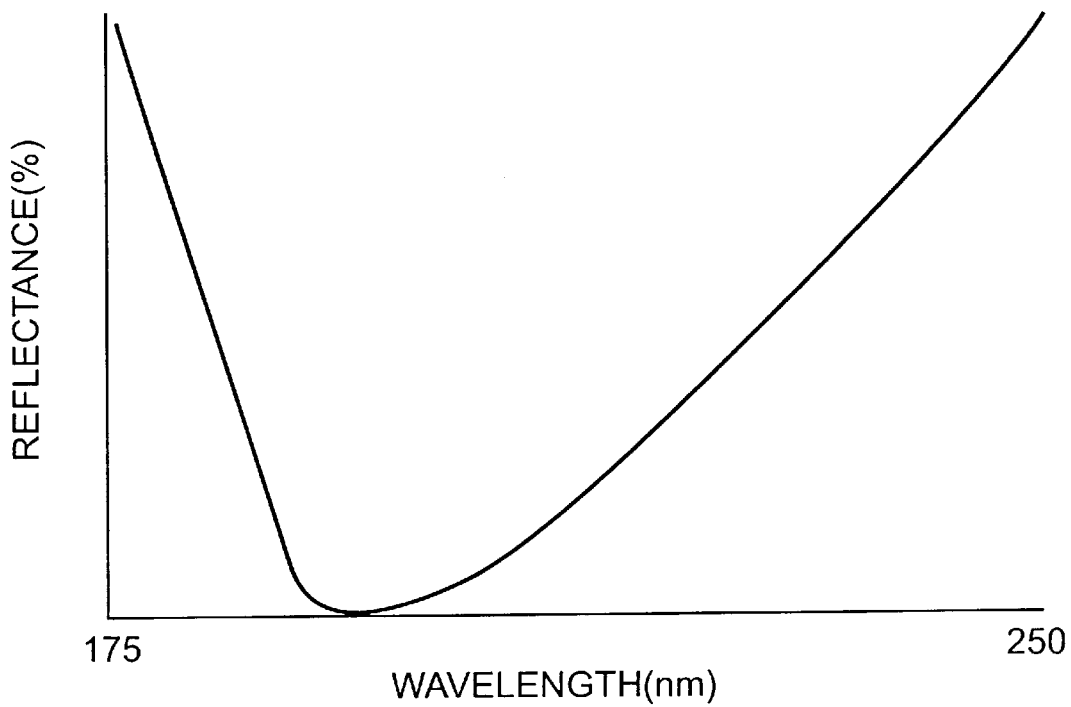
FIG. 24 is an explanatory drawing showing a measurement result achieved in the eighth embodiment of the present invention.
Figure 25:
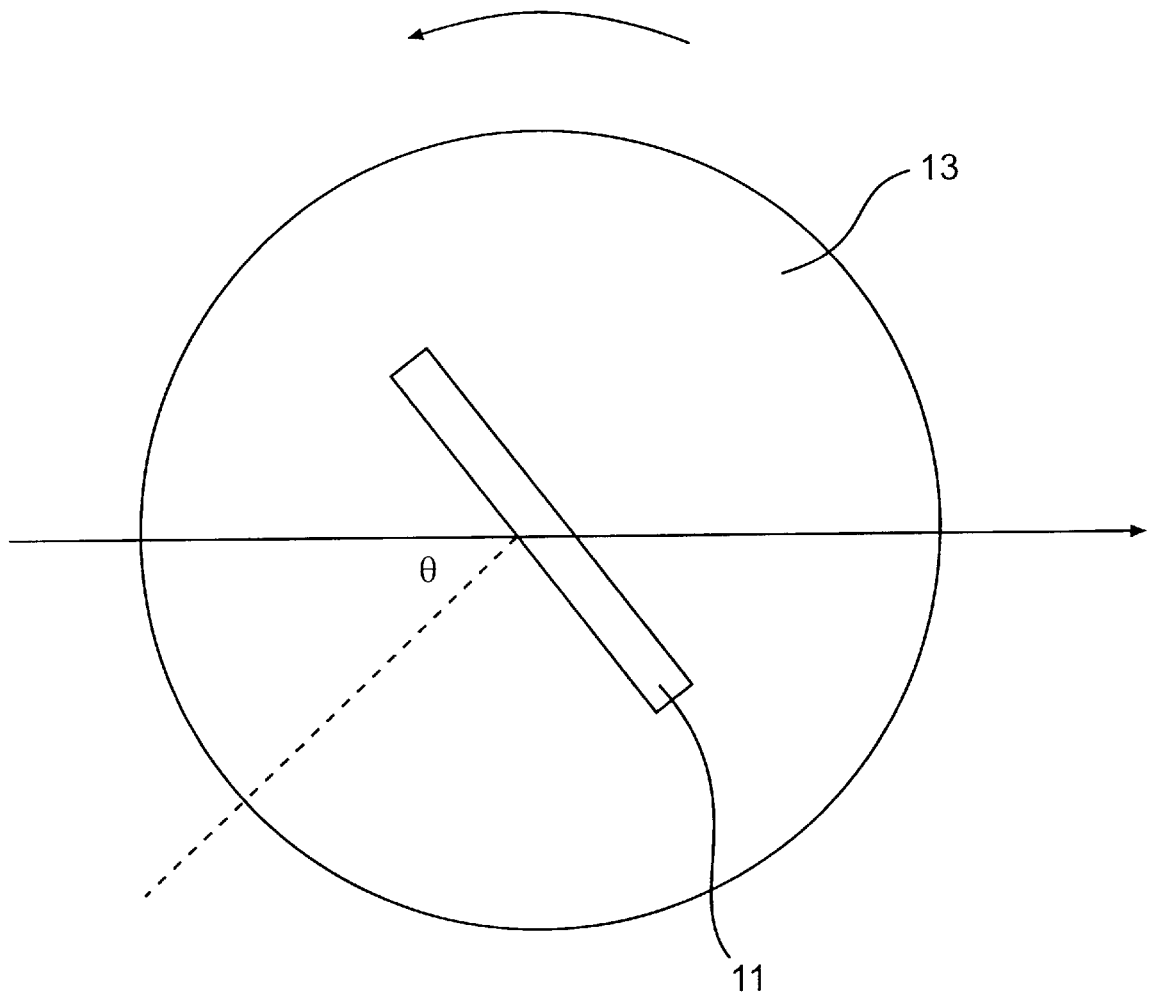
FIG. 25 is an explanatory drawing showing a conventional transmittance measuring device.
Figure 26A:
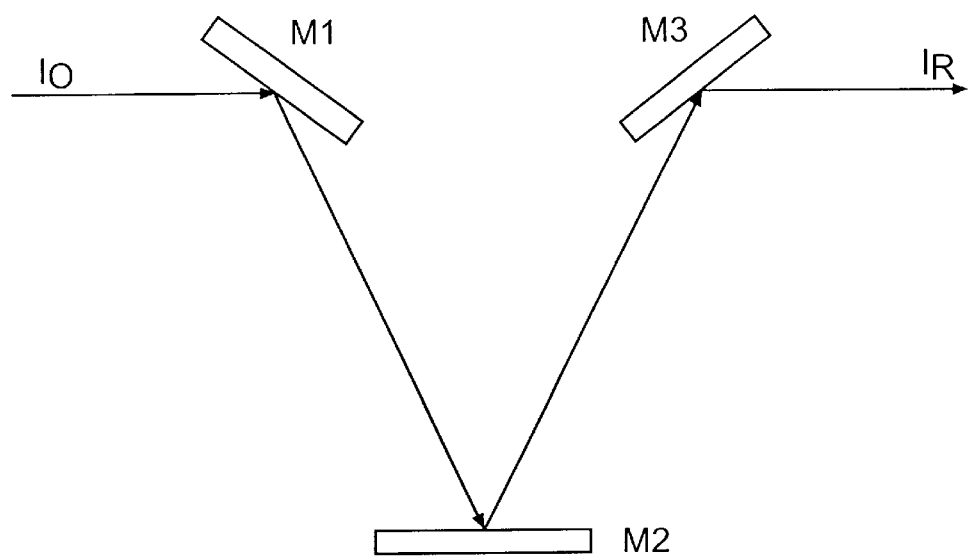
FIGS. 26A and 26B are explanatory drawings showing a conventional absolute reflectance measuring device.
Figure 26B:
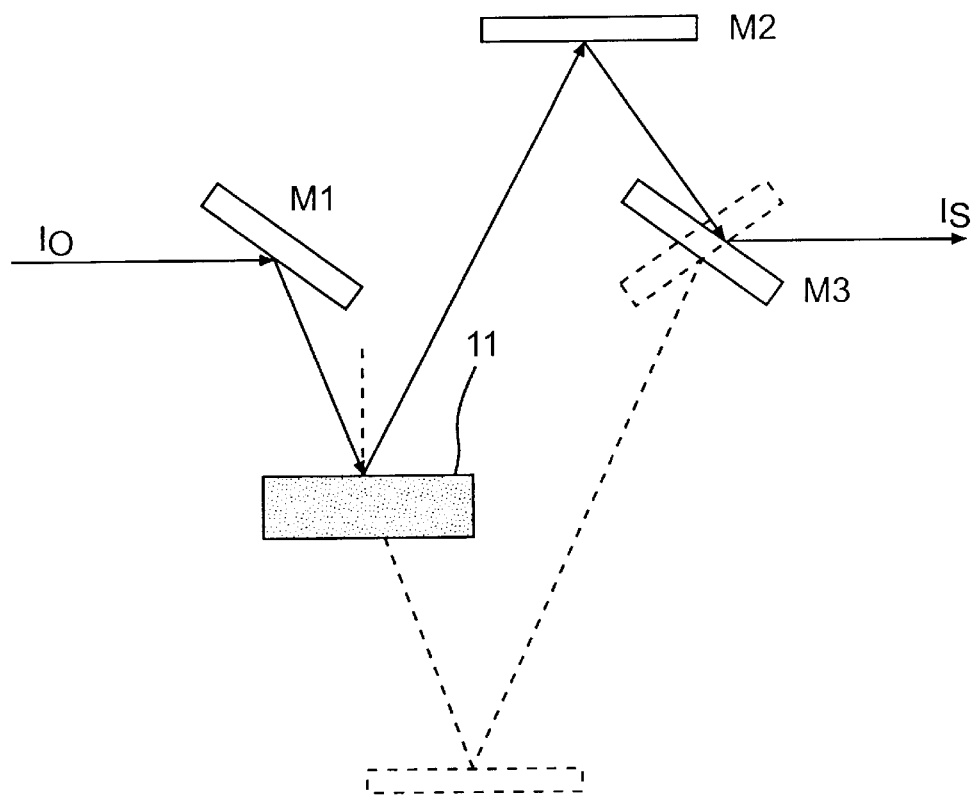
Figure 27A:
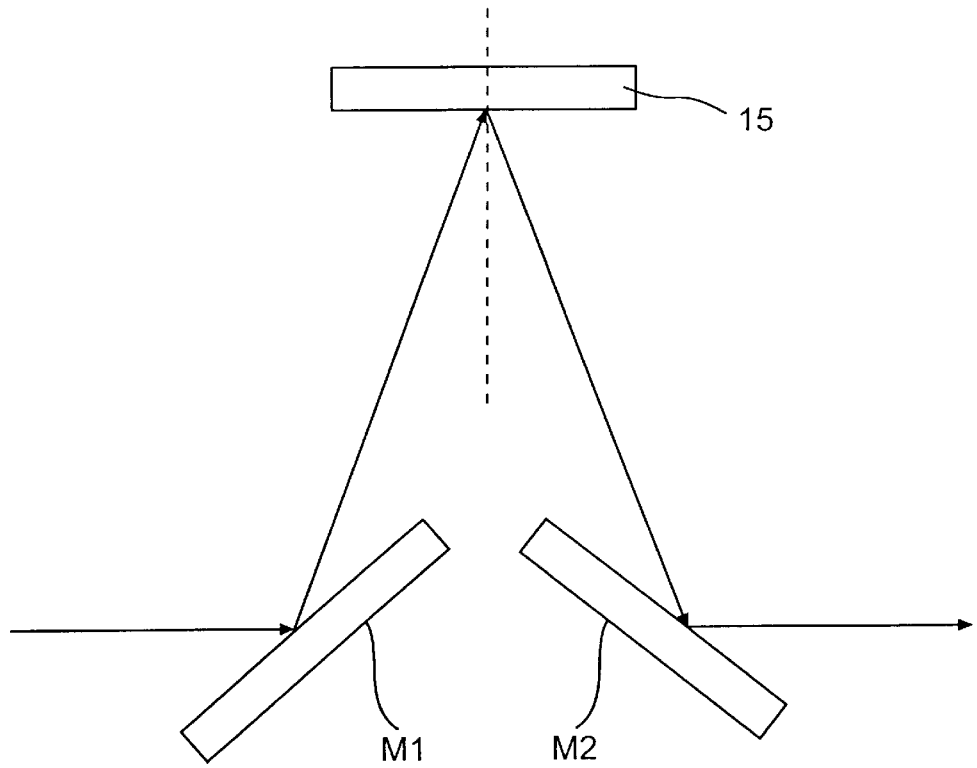
FIGS. 27A and 27B are explanatory drawings showing a conventional relative reflectance measuring device.
Figure 27B:
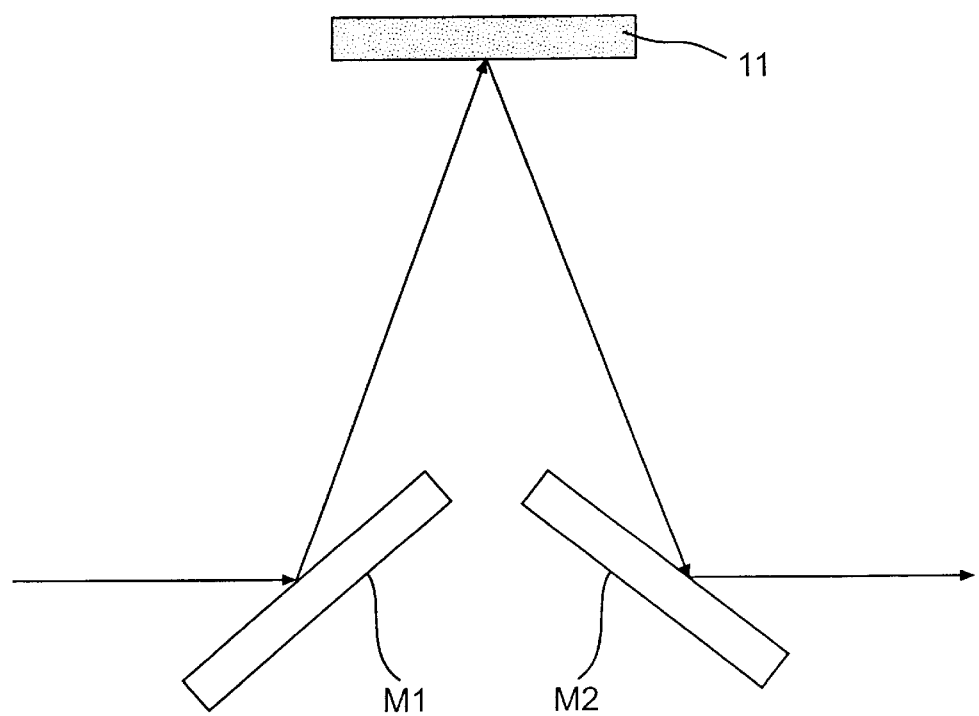
Figure 28:
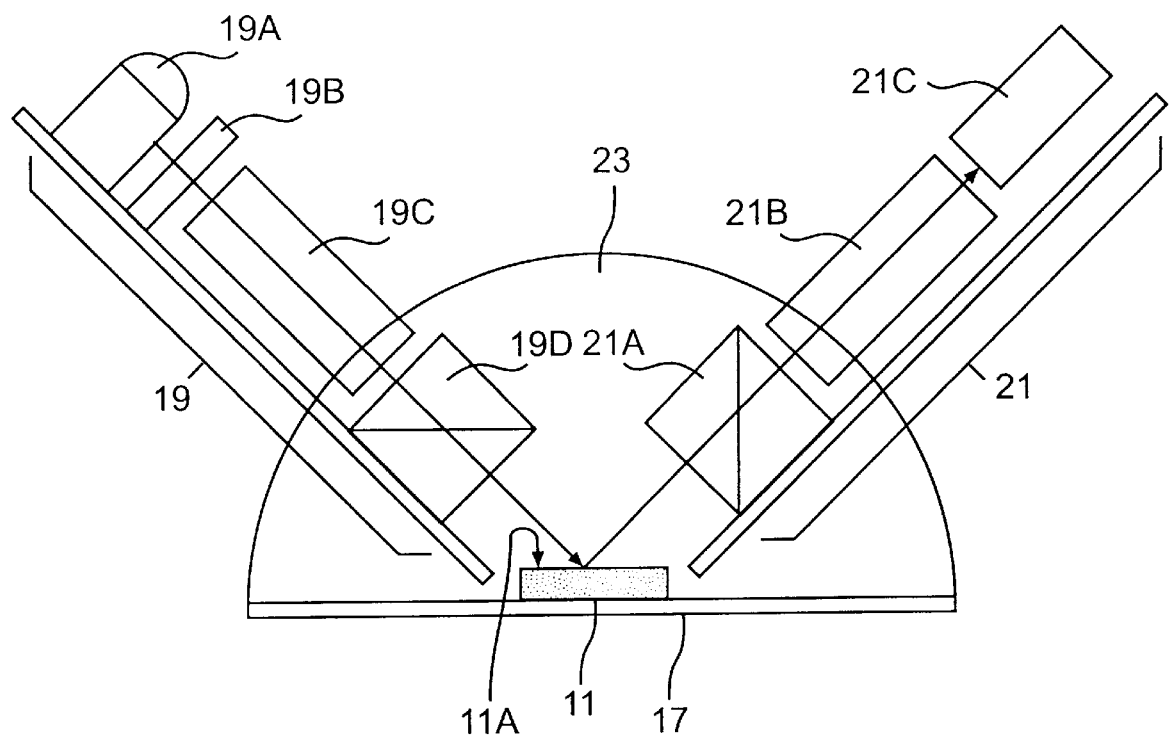
FIG. 28 is an explanatory drawing showing a conventional ellipsometer.

In example 8, relative reflectance of thin film is measured. The thin film is formed on a quartz base plate that has a diameter of 20 mm and a thickness of 2 mm. Firstly, the intensity lr of the exit light is measured using the optical system as shown in FIG. 5(A), in a state where the object 39, i.e., the quartz base plate without the thin film, is inserted into the optical system. The incident light L1 is p-polarized light of which wavelength ranges from 175 to 250 nm, and an angle of incidence on the quartz base plate is 30 degrees. Then, the intensity ls of the exit light is measured as shown in FIG. 5(B), in a state where the object 33, i.e., the quartz base plate with the thin film, is inserted into the optical system. From these measured lr and ls, the reflectance ls/lr is calculated. FIG. 24 is a graph of this reflectance. The horizontal axis of the graph is wavelength, and the vertical axis is reflectance. Thus, according to the present invention, wavelength dependence of relative reflectance of thin film can be determined.

Example 9

In example 9, phase change in reflection of thin film is measured. The thin film is formed on a quartz base plate that has a diameter of 20 mm and a thickness of 10 mm. Firstly, phase property $\phi r(\theta)$ is measured using the optical system as shown in FIG. 5(A), in a state where the object 39, i.e., the quartz base plate without thin film, is inserted into the optical system. The incident light L1 is p-polarized light having a wavelength of 190 nm, and is incident on the quartz base plate at an angle of incidence of 30, 50 and 60 degrees. Then, the object 33, i.e., the quartz base plate with the thin film, is inserted into the optical system as shown in FIG. 5(B), and phase property $\phi s(\theta)$ is measured as well as the phase property $\phi r(\theta)$. From these measured $\phi r(\theta)$ and $\phi s(\theta)$, the phase change in transmission of thin film $\Phi s = \phi s(\theta) - \phi r(\theta)$ is calculated. From this calculated $\Phi s$, refractive index and absorption constant of the object is determined.

Thus, according to the ninth example of the present invention, the phase change in reflection of thin film can be determined.

Example 10

In FIG. 16, the ellipsometer using double beam method is shown in a state of the first measurement. In example 10, however, the reference optical path 101 and the sample optical path 103 are set in a state of the second measurement Wherein light travels the optical path connecting the reflecting surfaces M1, M5, M6 and M4. At the neighborhood of the optical center on the sample optical path 103, the object, i.e., a quartz rectangular parallelepiped having a length of 20 mm, a width of 20 mm and a thickness of 50 mm, is placed. A wavelength of the incident light ranges from 175 nm to 250 nm. Then, the intensity of light lr exiting from the reference optical path 101, and the intensity of light ls exiting from the sample optical path 103 are measured. From these measured lr and ls, transmittance ls/lr is calculated. Thus, according to the 10th example of the present invention, desired transmittance can be determined.

Example 11

Referring to FIG. 16, the ellipsometer using double beam method is shown. In example 11, the reference optical path 101 and the sample optical path 103 are set in a state of the first measurement wherein light travels the optical path extending from the reflecting surface M1 to the reflecting surface M4, as shown in FIG. 16. At the neighborhood of the optical center of the sample optical path 103, the object, i.e., thin film formed on a quartz base plate having a diameter of 20 mm and a thickness of 2 mm, is placed (not shown). The incident light is p-polarized light having a wavelength of 250 nm, and is incident on the thin film at an angle between 5 and 30 degrees. Then, the intensity of light lr exiting from the reference optical path 101, and the intensity of light ls exiting from the sample optical path 103 are measured. From these measured lr and ls, transmittance ls/lr is calculated. Thus, according to the 11th example of the present invention, desired transmittance can be determined.

Example 12

Referring to FIG. 16, the ellipsometer using double beam method is shown. In example 12, the reference optical path 101 and the sample optical path 103 are set in a state of the first measurement wherein light travels the optical path extending from the reflecting surface M1 to the reflecting surface M4, as shown in FIG. 16. At the neighborhood of the optical center of the sample optical path 103, the object, i.e., thin film formed on a quartz base plate having a diameter of 20 mm and a thickness of 2 mm, is placed (not shown). The incident light is p-polarized light having a wavelength ranging from 175 to 250 nm, and is incident on the thin film at an angle of 30 degrees. Then, the intensity of light lr exiting from the reference optical path 101, and the intensity of light ls exiting from the sample optical path 103 are measured. From these measured lr and ls, transmittance ls/lr is calculated. Thus, according to the 12th example of the present invention, desired transmittance can be determined.

Example 13

Referring to FIG. 16, the ellipsometer using double beam method is shown. In example 13, the reference optical path 101 is set in the N state as shown in FIG. 16, and the sample optical path 103 is set in the non-N state as shown in FIG.

4(C). At the neighborhood of the optical center of the sample optical path 103, the object, i.e., a mirror (not shown) formed on a quartz base plate having a diameter of 20 mm and a thickness of 2 mm, is placed. The incident light is p-polarized light having a wavelength of 190 nm, and is incident on the mirror at an angle between 35 and 55 degrees. Then, the intensity of light lr exiting from the reference optical path 101, and the intensity of light ls exiting from the sample optical path 103 are measured. From these measured lr and ls, reflectance ls/lr is calculated. Thus, according to the 13th example of the present invention, desired reflectance can be determined.

Example 14

Referring to FIG. 16, the ellipsometer using double beam method is shown. In example 14, the reference optical path 101 is set in the N state as shown in FIG. 16, and the sample optical path 103 is set in the non-N state as shown in FIG. 4(C). At the neighborhood of the optical center of the sample optical path 103, the object, i.e., a mirror (not shown) formed on a quartz base plate having a diameter of 20 mm and a thickness of 2 mm, is placed. The incident light is p-polarized light having a wavelength ranging from 175 to 250 nm, and is incident on the mirror at an angle of 45 degrees. Then, the intensity of light lr exiting from the reference optical path 101, and the intensity of light ls exiting from the sample optical path 103 are measured. From these measured lr and ls, reflectance ls/lr is calculated. Thus, according to the 14th example of the present invention, desired reflectance can be determined.

Example 15

Referring to FIG. 16, the ellipsometer using double beam method is shown. In example 15, the reference optical path 101 is set in the N state as shown in FIG. 16, and the sample optical path 103 is set in the non-N state as shown in FIG. 4(C). At the neighborhood of the optical center of the sample optical path 103, the object, i.e., anti-reflection film (not shown) formed on a quartz base plate having a diameter of 20 mm and a thickness of 2 mm, is placed. The incident light is p-polarized light having a wavelength ranging from 175 to 250 nm, and is incident on the anti-reflection film at an angle of 30 degrees. Then, the intensity of light lr exiting from the reference optical path 101, and the intensity of light ls exiting from the sample optical path 103 are measured. From these measured lr and ls, reflectance ls/lr is calculated. Thus, according to the 15th example of the present invention, desired reflectance can be determined.

Example 16

Referring to FIG. 16, the ellipsometer using double beam method is shown. In example 16, the reference optical path 101 and the sample optical path 103 are set in the non-N state as shown in FIG. 4(C). At the neighborhood of the optical center of the sample optical path 103, the object, i.e., anti-reflection film (not shown) formed on a quartz base plate having a diameter of 20 mm and a thickness of 2 mm, is placed. And, at the neighborhood of the optical center of the sample optical path 101, the object, i.e., a quartz base plate without the anti-reflection film, is placed. The incident light is p-polarized light having a wavelength of 190 nm, and is incident on the anti-reflection film at an angle between 15 and 45 degrees. Then, the intensity of light lr exiting from the reference optical path 101, and the intensity of light ls exiting from the sample optical path 103 are measured. From these measured lr and ls, reflectance ls/lr is calculated. Thus, according to the 16th example of the present invention, desired reflectance can be determined.

Example 17

Referring to FIG. 16, the ellipsometer using double beam method is shown. In example 17, the reference optical path 101 and the sample optical path 103 are set in the non-N state as shown in FIG. 4(C). At the neighborhood of the optical center of the sample optical path 103, the object, i.e., thin film (not shown) formed on a quartz base plate having a diameter of 20 mm and a thickness of 2 mm, is placed. And, at the neighborhood of the optical center of the sample optical path 101, the object, i.e., a quartz base plate without the thin film, is placed. The light of incidence is p-polarized light having a wavelength of 190 nm, and is incident on the anti-reflection film at an angle of 30, 45 and 60 degrees. Then, the phase change property $\phi r\ (\theta)$ regarding the reference optical path 101, and the phase change property $\phi s\ (\theta)$ regarding the sample optical path 103 are measured. From these measured $\phi r\ (\theta)$ and $\phi s\ (\theta)$, phase change $\Phi s\ (\theta) = \phi s\ (\theta) - \phi r\ (\theta)$ is calculated. Thus, according to the 17th example of the present invention, phase change of light, refractive index and absorption constant of thin film in reflection can be determined.

What is claimed is:

1. A unit for measuring optical properties comprising:

a first through sixth reflecting surfaces for reflecting light of incidence by the first through fourth reflecting surfaces in first measurement, and for reflecting light of incidence by the first, the fifth, the sixth and the fourth reflecting surface in second measurement;

a reflecting surface rotating device for rotating the first and fourth reflecting surfaces; and an object moving device for inserting and extracting the object at a place between the second and third reflecting surfaces, or between the fifth and sixth reflecting surfaces, wherein the first through fourth reflecting surfaces are arranged so that light traveling from the first through fourth reflecting surfaces draws an "N"-like light path, and so that the light of incidence on the first reflecting surface has the same optical axis as the light exiting from the fourth reflecting surface, each of the first and fourth reflecting surfaces is arranged so that each of the first and fourth reflecting surfaces is perpendicular to a plane containing the "N"-like light path, the second reflecting surface is defined as a first ellipsoid of revolution having foci of an optical center O and a point of incidence A, wherein the point of incidence A is a point at which the light of incidence impinges on the first reflecting surface, and the optical center O is a point that a line segment AD, which connects the point of incidence A with a point D that is an exit point on the fourth reflecting surface, intersects a light path between the second reflecting surface and the third reflecting surface, the third reflecting surface is defined as a second ellipsoid of revolution having foci of the optical center O and the exit point D, the fifth reflecting surface makes the reflected light from the first reflecting surface parallel, the sixth reflecting surface converges the reflected light from the fifth reflecting surface onto the fourth reflecting surface, the reflecting surface rotating device rotates the first and fourth reflecting surfaces at each of their positions about each axis perpendicular to the plane containing the N-like light path, the fourth reflecting surface operating with the first reflecting surface, the object moving device selectively sets either an insertion state or a non-insertion state, the insertion state being a state that the object is inserted to a position between the second and third reflecting surfaces, or between the fifth and sixth reflecting surfaces, so that a measuring surface of the object contains the optical center, and the non-insertion state being a state that the object is extracted from the position.

2. A unit for measuring optical properties according to claim 1, wherein the second measurement is measurement that measures a transmittance of a thick object.

3. A unit for measuring optical properties according to claim 2, further comprising: a reflecting surface moving device that selectively creates either of an N state or a non-N state, the N state being a state where "N"-like light path is formed by arranging the third and fourth reflecting surfaces, the non-N state being a state where a light path other than "N"-like light path is formed by arranging the third and fourth reflecting surfaces being rotated 180 degrees about the line segment relative to N state.

4. A unit for measuring optical properties according to claim 3, further comprising: a seventh reflecting surface that has a corresponding shape to the third reflecting surface and is arranged at a corresponding position of the third reflecting surface in the non-N state, wherein the reflecting surface moving device is replaced by a reflecting surface moving device which moves only fourth reflecting mirror in order to create the N state or the non-N state.

5. A unit for measuring optical properties according to claim 1, wherein the fifth reflecting surface is a first parabolic mirror that is arranged at a position such that the fifth reflecting surface makes light reflected from the first reflecting surface parallel and pass through the optical center O, and the sixth reflecting surface is a second parabolic mirror that is arranged at a position such that the sixth reflecting surface makes light reflected from the first parabolic mirror converge on the fourth reflecting surface.

6. A unit for measuring optical properties according to claim 5, further comprising: a reflecting surface moving device that selectively creates either of an N state or a non-N state, the N state being a state where "N"-like light path is formed by arranging the third and fourth reflecting surfaces, the non-N state being a state where a light path other than "N"-like light path is formed by arranging the third and fourth reflecting surfaces being rotated 180 degrees about the line segment relative to N state.

7. A unit for measuring optical properties according to claim 6, further comprising: a seventh reflecting surface that has a corresponding shape to the third reflecting surface and is arranged at a corresponding position of the third reflecting surface in the non-N state, wherein the reflecting surface moving device is replaced by a reflecting surface moving device which moves only fourth reflecting mirror in order to create the N state or the non-N state.

8. A unit for measuring optical properties according to claim 1, wherein each of the second and third reflecting surfaces has a shape of a cylindrical ellipse that has no curvature in a direction perpendicular to the plane containing the "N"-like light path, or has a shape of a sphere that has the approximately same shape as the ellipsoid of revolution, instead of forming the ellipsoid of revolution.

9. A unit for measuring optical properties according to claim 8, further comprising: a reflecting surface moving device that selectively creates either of an N state or a non-N state, the N state being a state where "N"-like light path is formed by arranging the third and fourth reflecting surfaces, the non-N state being a state where a light path other than "N"-like light path is formed by arranging the third and fourth reflecting surfaces being rotated 180 degrees about the line segment relative to N state.

10. A unit for measuring optical properties according to claim 9, further comprising: a seventh reflecting surface that has a corresponding shape to the third reflecting surface and is arranged at a corresponding position of the third reflecting surface in the non-N state, wherein the reflecting surface moving device is replaced by a reflecting surface moving device which moves only fourth reflecting mirror in order to create the N state or the non-N state.

11. A unit for measuring optical properties according to claim 1, wherein the reflecting surface rotating device rotates the first reflecting surface and the fourth reflecting surface about the line segment AD that connects the point of incidence A with the exit point D, the fourth reflecting surface operating with the first reflecting surface.

12. A unit for measuring optical properties according to claim 11, further comprising: a reflecting surface moving device that selectively creates either of an N state or a non-N state, the N state being a state where "N"-like light path is formed by arranging the third and fourth reflecting surfaces, the non-N state being a state where a light path other than "N"-like light path is formed by arranging the third and fourth reflecting surfaces being rotated 180 degrees about the line segment relative to N state.

13. A unit for measuring optical properties according to claim 12, further comprising: a seventh reflecting surface that has a corresponding shape to the third reflecting surface and is arranged at a corresponding position of the third reflecting surface in the non-N state, wherein the reflecting surface moving device is replaced by a reflecting surface moving device which moves only fourth reflecting mirror in order to create the N state or the non-N state.

14. A unit for measuring optical properties according to claim 1, further comprising: a reflecting surface moving device that selectively creates either of an N state or a non-N state, the N state being a state where "N"-like light path is formed by arranging the third and fourth reflecting surfaces, the non-N state being a state where a light path other than "N"-like light path is formed by rotating the third and fourth reflecting surfaces 180 degrees about the line segment relative to N state.

15. A unit for measuring optical properties according to claim 14, further comprising: a seventh reflecting surface that has a corresponding shape to the third reflecting surface and is arranged at a corresponding position of the third reflecting surface in the non-N state, wherein the reflecting surface moving device is replaced by a reflecting surface moving device which moves only fourth reflecting mirror in order to create the N state or the non-N state.

* * * * *